(12) United States Patent
Wang et al.

(10) Patent No.: US 10,017,438 B2
(45) Date of Patent: Jul. 10, 2018

(54) METHOD AND DEVICE SYSTEM FOR PRODUCING DIMETHYL OXALATE THROUGH CARBONYLATION OF INDUSTRIAL SYNTHESIS GAS AND PRODUCING ETHYLENE GLYCOL THROUGH DIMETHYL OXALATE HYDROGENATION

(71) Applicant: SHANGHAI WUZHENG ENGINEERING TECHNOLOGY CO., LTD., Shanghai (CN)

(72) Inventors: Baoming Wang, Shanghai (CN); Donghui Wang, Shanghai (CN); Yujiang Li, Shanghai (CN); Changqing Xu, Shanghai (CN)

(73) Assignee: SHANGHAI WUZHENG ENGINEERING TECHNOLOGY CO., LTD., Shanghai (CN)

( * ) Notice: Subject to any disclaimer, the term of this patent is extended or adjusted under 35 U.S.C. 154(b) by 31 days.

(21) Appl. No.: 15/316,178

(22) PCT Filed: Jul. 23, 2014

(86) PCT No.: PCT/CN2014/082837
§ 371 (c)(1),
(2) Date: Jun. 7, 2017

(87) PCT Pub. No.: WO2015/184677
PCT Pub. Date: Dec. 10, 2015

(65) Prior Publication Data
US 2017/0267615 A1    Sep. 21, 2017

(30) Foreign Application Priority Data

Jun. 5, 2014    (CN) .......................... 2014 1 02469786
Jun. 5, 2014    (CN) .................. 2014 2 02967486 U

(51) Int. Cl.
*C07C 67/00*    (2006.01)
*C07C 29/151*    (2006.01)
*C07C 67/36*    (2006.01)
*B01J 8/02*    (2006.01)

(52) U.S. Cl.
CPC ............... *C07C 29/151* (2013.01); *B01J 8/02* (2013.01); *B01J 8/0278* (2013.01); *C07C 67/36* (2013.01); *B01J 2208/027* (2013.01)

(58) Field of Classification Search
CPC ...... B01J 2208/027; B01J 8/02; B01J 8/0278; C07C 29/151; C07C 67/36; Y02P 20/121
See application file for complete search history.

(56) References Cited

FOREIGN PATENT DOCUMENTS

| CN | 101462961 | * | 6/2009 |
|---|---|---|---|
| CN | 101462961 | A | 6/2009 |
| CN | 101830806 | A | 9/2010 |
| CN | 104098441 | A | 10/2014 |

* cited by examiner

*Primary Examiner* — Yevgeny Valenrod
*Assistant Examiner* — Blaine G Doletski
(74) *Attorney, Agent, or Firm* — Global IP Services; Tianhua Gu

(57) ABSTRACT

A method and a device system for producing dimethyl oxalate through high-pressure carbonylation of industrial synthesis gases and producing ethylene glycol through dimethyl oxalate hydrogenation. The method comprises the following steps: adopting industrial NO, $O_2$ and methanol as raw materials to perform an esterification reaction to produce methyl nitrite, then adopting industrial CO and methyl nitrite to perform a carbonylation reaction in a plate reactor to produce carbonylation products which mainly include dimethyl oxalate and dimethyl carbonate, separating the carbonylation products to obtain dimethyl carbonate products, and subsequently performing hydrogenation to dimethyl oxalate in the plate reactor to produce ethylene glycol products; and performing coupling recovery treatment to waste acid in the esterification reaction and purge gas in the carbonylation reaction for recycling. The system comprises an esterification reaction system, a carbonylation reaction system, a purge gases and waste acid coupling recovery system and a hydrogenation reaction system.

42 Claims, 2 Drawing Sheets

METHOD AND DEVICE SYSTEM FOR PRODUCING DIMETHYL OXALATE THROUGH CARBONYLATION OF INDUSTRIAL SYNTHESIS GAS AND PRODUCING ETHYLENE GLYCOL THROUGH DIMETHYL OXALATE HYDROGENATION

CROSS REFERENCE TO RELATED PATENT APPLICATION

The present application is the US national stage of PCT/CN2014/082837 filed on Jul. 23, 2014, which claims the priorities of the Chinese patent applications No. 2014202967486 filed on Jun. 5, 2014 and No. 2014102469786 filed on Jun. 5, 2014, which applications are incorporated herein by reference.

BACKGROUND OF THE PRESENT INVENTION

Field of Invention

The present invention relates to a method and a device system for producing ethylene glycol through industrial synthesis gas, in particular to a method and a device system for producing dimethyl oxalate through high-pressure carbonylation of industrial synthesis gas and producing ethylene glycol through dimethyl oxalate hydrogenation.

Description of Related Arts

Ethylene glycol is a chemical which is widely used, is mainly applied in various production fields of polyester fibers (PET), anti-freezing agents, ethanolamine, explosives, etc., and is used in a great amount as solvent, lubricant and plasticizer. The application proportion of ethylene glycol in the PET polyester industry is close to 95%. At present, ethylene glycol is produced in industry mainly by adopting a route of producing ethylene oxide through gas phase oxidation of petro-ethylene and then producing ethylene glycol through liquid phase catalytic hydration. However, since the international oil price is kept high for a long time in recent years, the industrial link of producing ethylene glycol by using ethylene as raw materials faces to a great pressure at present. Thus, a technical route of producing ethylene glycol by adopting synthesis gas is increasingly and widely concerned due to low production cost.

At present, a tubular reactor is mainly adopted in a method for producing ethylene glycol by using coal. However, there are common problems of low reaction heat transfer efficiency, low utilization coefficient and low packing coefficient of catalyst, such that the production capability of the reactor is influenced.

Patent (Publication No.: CN101462961) provides a method for producing ethylene glycol and coproducing dimethyl carbonate. This method comprises synthesizing dimethyl oxalate and dimethyl carbonate through CO and methyl nitrite, performing distillation separation to obtain dimethyl carbonate products and synthesizing ethylene glycol through catalytic hydrogenation of heavy components dimethyl oxalate, and further comprises performing regeneration reaction of methyl nitrite in the system. However, since a tubular reactor is used as a reactor, waste gas and waste liquid produced during reaction are not recycled and recovered, the energy consumption of the device is relatively high and the increasing national environmental protection requirements cannot be satisfied.

Patent (Publication No.: CN101830806) discloses a method and a device for coproducing dimethyl carbonate and dimethyl oxalate. In the patent, two carbonylation reactors are adopted, the first reactor is a dimethyl carbonate synthesis reactor, the second reactor is a dimethyl oxalate reactor, methyl nitrite produced through reaction respectively enters the two reactors to respectively produce dimethyl carbonate and dimethyl oxalate, and then the products are respectively separated and purified. To view from the angle of the method route design, it substantively involves simple accumulation of two types of reactors and the actual effect of coproducing DMO and DMC in the same device cannot be actually realized. In the patent, energy optimization is not performed to the overall method flow and environmental protection measures which are necessary to be taken during reaction are not disclosed, either. The method is just an experimental method instead of an industrialized method.

Moreover, the loss of NO in the exhaust process and the production of nitric acid byproducts in the treatment reaction method are tough problems. Patent CN201210531022.1 discloses a method, in which the produced nitric acid is concentrated, and then part of NO-containing recycled gas is used to react therewith to produce $NO_2$ which is returned back to the methyl nitrite regeneration reactor. However, the NO-containing recycled gas further contains a great amount of gases such as methyl nitrite and methanol which will also react with the concentrated nitric acid, such that the products are complex and the efficiency of the device is influenced.

To sum up, the existing method for producing ethylene glycol by using coal mainly has the problems that the catalyst utilization rate is low, the catalyst packing coefficient is low, the valuable gases in the device cannot be fully utilized but pollute the environment, the heat of the device system cannot be fully utilized and thereby the social and economic benefits are not ideal.

SUMMARY OF THE PRESENT INVENTION

The purpose of the present invention is to provide a method and a device system for improving production capacity of a single-series device and realizing tail gas treatment, byproduct recovery and raw material comprehensive utilization, so as to solve the problems that the raw material utilization rate is low, the production cost is great, the catalyst utilization rate is low, the packing coefficient is low, the equipment investment is too great, single-series equipment cannot adapt to device enlargement, the system consumption is great, the device cannot satisfy the increasingly strict national requirements on industrial environments during using and the like in the current method for producing ethylene glycol.

The present invention is implemented through the following technical solution:

A device system for producing dimethyl oxalate through high-pressure carbonylation of industrial synthesis gas and producing ethylene glycol through dimethyl oxalate hydrogenation comprises a carbonylation reaction system, an esterification reaction system, a purge gas and waste acid coupled recovery system and a hydrogenation reaction system;

the carbonylation reaction system comprises a carbonylation reactor, a first gas-liquid separator, a methanol washing tower, a methanol rectification tower and a DMO rectification tower; the carbonylation reactor is provided with a top feed inlet, a bottom discharge outlet, a bottom coolant inlet and a top coolant outlet; the first gas-liquid separator is provided with a feed inlet, a gas outlet and a liquid outlet; the methanol washing tower is provided with an upper feed inlet, a lower feed inlet, a top outlet and a bottom outlet; the methanol rectification tower is provided with an upper feed inlet, a lower feed inlet, a top outlet and a bottom outlet; the DMO rectification tower is provided with a lower feed inlet, a top outlet and a bottom outlet;

the esterification reaction system comprises an esterification reaction tower and a methanol recovery tower; the esterification reaction tower is provided with a top feed inlet, an upper feed inlet, a plurality of lower feed inlets, a middle reflux inlet, a top outlet and a bottom outlet; the methanol recovery tower is provided with a middle-lower feed inlet, a lower feed inlet, a top outlet and a bottom outlet;

the purge gas and waste acid coupled recovery system comprises a nitric acid concentration tower, an NO recovery tower, an MN recovery tower and a pressure swing adsorption tank; the nitric acid concentration tower is provided with a middle feed inlet, a top outlet and a bottom outlet; the NO recovery tower is provided with a top feed inlet, a middle feed inlet, a bottom feed inlet, a top outlet and a bottom outlet; the MN recovery tower is provided with an upper feed inlet, a lower feed inlet, a top outlet and a bottom outlet; the pressure swing adsorption tank is provided with a feed inlet, a recovered gas outlet and an exhaust gas outlet;

the hydrogenation reaction system comprises a hydrogenation recycle compressor, a hydrogenation reactor, a second gas-liquid separator, a membrane separator, a methanol separation tower, a light component rectification tower and an ethylene glycol product tower; the hydrogenation recycle compressor comprises an inlet and an outlet; the hydrogenation reactor is provided with a top feed inlet, a bottom discharge outlet, a bottom coolant inlet and a top coolant outlet; the second gas-liquid separator is provided with a feed inlet, a gas outlet and a liquid outlet; the membrane separator is provided with a feed inlet, a recovered gas outlet and an exhaust gas outlet; the methanol separation tower is provided with a middle feed inlet, a top non-condensable gas outlet, a top liquid phase light component outlet and a bottom liquid phase heavy component outlet; the light component rectification tower is provided with a lower feed inlet, a top outlet and a bottom outlet; the ethylene glycol product tower is provided with a lower feed inlet, a top outlet, an upper outlet and a bottom outlet;

the top feed inlet of the carbonylation reactor is connected to a CO raw material pipe and an $N_2$ raw material pipe through a pipeline; the bottom discharge outlet of the carbonylation reactor is connected to the feed inlet of the first gas-liquid separator through a pipeline; the gas outlet of the first gas-liquid separator is connected to the lower feed inlet of the methanol washing tower through a pipeline; the liquid outlet of the first gas-liquid separator is connected to the upper feed inlet of the methanol rectification tower through a pipeline; the top outlet of the methanol washing tower is provided with a branch outlet A and a branch outlet B, the branch outlet A is connected to one lower feed inlet of the esterification reaction tower through a pipeline, and the branch outlet B is connected to the bottom feed inlet of the NO recovery tower through a pipeline; the bottom outlet of the methanol washing tower is connected to the lower feed inlet of the methanol rectification tower through a pipeline; the top outlet of the methanol rectification tower is connected to the upper feed inlet of the esterification reaction tower through a pipeline; the bottom outlet of the methanol rectification tower is connected to the lower feed inlet of the DMO rectification tower through a pipeline; the bottom outlet of the DMO rectification tower is connected to the top feed inlet of the hydrogenation reactor through a pipeline, and the top outlet of the DMO rectification tower is a DMC product outlet;

the other lower feed inlets of the esterification reaction tower are respectively connected to an NO raw material pipe and a plurality of $O_2$ raw material pipes through pipelines; the top feed inlet of the esterification reaction tower is connected to a methanol raw material pipe through a pipeline; the bottom outlet of the esterification reaction tower is provided with a branch outlet C and a branch outlet D, the branch outlet C is connected to the middle reflux inlet of the esterification reaction tower through a pipeline, and the branch outlet D is connected to the lower feed inlet of the methanol recovery tower through a pipeline; the top outlet of the esterification reaction tower is connected to the top feed inlet of the carbonylation reactor through a pipeline; the top outlet of the methanol recovery tower is provided with a branch outlet E and a branch outlet F, the branch outlet E is connected to the upper feed inlet of the esterification reaction tower through a pipeline, and the branch outlet F is connected to the upper feed inlet of the MN recovery tower through a pipeline; the bottom outlet of the methanol recovery tower is connected to the middle feed inlet of the nitric acid concentration tower through a pipeline;

the top outlet of the nitric acid concentration tower is a waste liquid drain outlet; the bottom outlet of the nitric acid concentration tower is connected to the middle feed inlet of the NO recovery tower through a pipeline; the top outlet of the NO recovery tower is connected to the lower feed inlet of the MN recovery tower through a pipeline; the bottom outlet of the NO recovery tower is connected to the middle-lower feed inlet of the methanol recovery tower through a pipeline; the top outlet of the MN recovery tower is connected to the feed inlet of the pressure swing adsorption tank through a pipeline; the bottom outlet of the MN recovery tower is connected with the upper feed inlet of the esterification reaction tower through a pipeline; the recovered gas outlet of the pressure swing adsorption tank is connected to the top feed inlet of the carbonylation reactor through a pipeline; the exhaust gas outlet of the pressure swing adsorption tank is connected to an external recovery device through a pipeline;

the inlet of the hydrogenation recycle compressor is connected to an industrial hydrogen raw material pipe through a pipeline, and the outlet of the hydrogenation recycle compressor is connected to the top feed inlet of the hydrogenation reactor through a pipeline; the bottom discharge outlet of the hydrogenation reactor is connected to the feed inlet of the second gas-liquid separator through a pipeline; the gas outlet of the second gas-liquid separator is provided with a branch outlet G and a branch outlet H, the branch outlet G is connected to the inlet of the hydrogenation recycle compressor through a pipeline, and the branch outlet H is connected to the feed inlet of the membrane separator through a pipeline; the liquid outlet of the second gas-liquid separator is connected to the lower feed inlet of the methanol separation tower through a pipeline; the top non-condensable gas outlet of the methanol separation tower is connected to the feed inlet of the membrane separator through a pipeline; the top liquid phase light component outlet of the methanol separation tower is provided with a branch outlet I and a branch outlet J, the branch outlet I is connected to the upper feed inlet of the methanol washing tower through a pipeline, and the branch outlet J is connected to the top feed inlet of the NO recovery tower through a pipeline; the bottom liquid phase heavy component outlet of the methanol separation tower is connected to the lower feed inlet of the light component rectification tower through a pipeline; the top light component outlet of the light component rectification tower is connected to an external methanol recovery device through a pipeline; the bottom heavy component outlet of the light component rectification tower is connected to the lower feed inlet of the ethylene glycol product tower through a pipeline; the top outlet of the ethylene glycol product tower is connected to an external 1,2-BDO recovery treatment device through a pipeline; the bottom outlet of the ethylene glycol product tower is connected to an external recovery treatment device through a pipeline; the upper outlet of the ethylene glycol product tower is an ethylene glycol product outlet; and the exhaust gas outlet of the membrane separator is connected to an external recovery device through a pipeline, and the recovered gas outlet of the membrane separator is connected to the top feed inlet of the hydrogenation reactor through a pipeline.

The carbonylation reactor is externally connected to a dehydration tower; the dehydration tower is provided with a feed inlet and a dried gas outlet; the top outlet of the esterification reaction tower and the recovered gas outlet of the pressure swing adsorption tank are connected to the feed inlet of the dehydration tower through pipelines; and the dried gas outlet of the dehydration tower is connected to the top feed inlet of the carbonylation reactor through a pipeline.

The dehydration tower consists of a molecular sieve dryer A and a molecular sieve dryer B which alternatively run and are regenerated; the molecular sieve dryer A and the molecular sieve dryer B are packed with adsorbents; and the adsorbents are selected from a group consisting of 3 A molecular sieve, 4 A molecular sieve, 5 A molecular sieve, 9 A molecular sieve and calcium oxide.

The bottom discharge outlet of the carbonylation reactor is connected to an outlet heat exchanger I; the outlet heat exchanger I is provided with a cold material flow inlet, a cold material flow outlet, a hot material flow inlet and a hot material flow outlet; the CO raw material pipe, the $N_2$ raw material pipe and the dried gas outlet of the dehydration tower are connected to the cold material flow inlet of the outlet heat exchanger I through pipelines; the cold material flow outlet of the outlet heat exchanger I is connected to the top feed inlet of the carbonylation reactor through a pipeline; the bottom discharge outlet of the carbonylation reactor is connected to the hot material flow inlet of the outlet heat exchanger I; and the hot material flow outlet of the outlet heat exchanger I is connected to the feed inlet of the first gas-liquid separator through a pipeline.

The carbonylation reactor is externally connected to a steam drum I; the steam drum I is provided with a coolant inlet, a coolant outlet, a steam-liquid mixture inlet and a steam outlet; the coolant inlet of the steam drum I is connected to a coolant raw material pipe through a pipeline; the coolant outlet of the steam drum I is connected to the bottom coolant inlet of the carbonylation reactor through a pipeline; the top coolant outlet of the carbonylation reactor is connected to the steam-liquid mixture inlet of the steam drum I through a pipeline; and the steam outlet of the steam drum I is connected to an external steam recovery system through a pipeline.

A carbonylation recycle compressor is connected between the branch outlet A of the methanol washing tower and the lower feed inlet of the esterification reaction tower; the carbonylation recycle compressor is provided with an inlet and an outlet; the branch outlet A is connected to the inlet of the carbonylation recycle compressor through a pipeline; and the outlet of the carbonylation recycle compressor is connected to the lower feed inlet of the esterification reaction tower through a pipeline.

A compressor is connected between the top outlet of the NO recovery tower and the bottom feed inlet of the MN recovery tower; the compressor is provided with an inlet and an outlet; the top outlet of the NO recovery tower is connected to the inlet of the compressor through a pipeline; and the outlet of the compressor is connected to the bottom feed inlet of the MN recovery tower through a pipeline.

The bottom discharge outlet of the hydrogenation rector is connected to an outlet heat exchanger II; the outlet heat exchanger II is provided with a cold material flow inlet, a cold material flow outlet, a hot material flow inlet and a hot material flow outlet; the bottom outlet of the DMO rectification tower, the recovered gas outlet of the membrane separator and the outlet of the hydrogenation recycle compressor are connected to the cold material flow inlet of the outlet heat exchanger II through pipelines; the cold material flow outlet of the outlet heat exchanger II is connected to the top feed inlet of the hydrogenation reactor through a pipeline; the bottom discharge outlet of the hydrogenation reactor is connected to the hot material flow inlet of the outlet heat exchanger II through a pipeline; and the hot material flow outlet of the outlet heat exchanger II is connected to the feed inlet of the second gas-liquid separator through a pipeline.

The top feed inlet of the hydrogenation reactor is connected to a startup heater the startup heater is provided with a feed inlet and a discharge outlet; the cold material flow outlet of the outlet heat exchanger II is connected to the feed inlet of the startup heater through a pipeline; and the discharge outlet of the startup heater is connected to the top feed inlet of the hydrogenation reactor through a pipeline.

The hydrogenation reactor is externally connected to a steam drum II the steam drum II is provided with a coolant inlet, a coolant outlet, a steam-liquid mixture inlet and a steam outlet; the coolant inlet of the steam drum II is connected to a coolant raw material pipe through a pipeline; the coolant outlet of the steam drum II is connected to the bottom coolant inlet of the hydrogenation reactor through a pipeline; the top coolant outlet of the hydrogenation reactor is connected to the steam-liquid mixture inlet of the steam drum II through a pipeline; and the steam outlet of the steam drum II is connected to an external steam recovery system through a pipeline.

The second gas-liquid separator comprises a high-pressure gas-liquid separator and a low-pressure gas-liquid separator; the high-pressure gas-liquid separator is provided with a feed inlet, a gas outlet and a liquid outlet; the low-pressure gas-liquid separator is provided with a feed inlet, a gas outlet and a liquid outlet; the hot material flow outlet of the outlet heat exchanger II is connected to the feed inlet of the high-pressure gas-liquid separator through a pipeline; the gas outlet of the high-pressure gas-liquid separator is provided with a branch outlet K and a branch outlet L, the branch outlet K is connected to the inlet of the hydrogenation recycle compressor through a pipeline, and the branch outlet L is connected to the feed inlet of the low-pressure gas-liquid separator through a pipeline; the liquid outlet of the high-pressure gas-liquid separator is connected to the middle feed inlet of the methanol separation tower through a pipeline; the gas outlet of the low-pressure gas-liquid separator is connected to the feed inlet of the membrane separator through a pipeline; and the liquid outlet of the low-pressure gas-liquid separator is connected to the middle feed inlet of the methanol separation tower through a pipeline.

A methanol absorption tank is provided in front of the feed inlet of the membrane separator; the methanol absorption tank is provided with a feed inlet and a purified gas outlet; the gas outlet of the low-pressure gas-liquid separator and the top non-condensable gas outlet of the methanol separation tower are connected to the feed inlet of the methanol absorption tank through pipelines; and the purified gas outlet of the methanol absorption tank is connected to the feed inlet of the membrane separator through a pipeline.

Preferably, the carbonylation reactor is a plate reactor, a tube reactor or a tube-plate combined reactor.

Preferably, the carbonylation reactor is a plate fixed-bed carbonylation reactor.

Preferably, a center of the plate fixed-bed carbonylation reactor is provided with a plate group fixing chamber, a plate group is provided in the plate group fixing chamber and the plate group fixing chamber is further provided with a bottom inlet and a top outlet; a catalyst bed layer is provided between an outer wall of the plate group fixing chamber and an inner wall of the plate fixed-bed carbonylation reactor; the catalyst bed layer is packed with a carbonylation reaction catalyst and the catalyst bed layer is further provided with a top inlet and a bottom outlet; at a bottom of the plate fixed-bed carbonylation reactor, a bottom coolant inlet of the plate fixed-bed carbonylation reactor is connected to the bottom inlet of the plate group fixing chamber through a pipeline, and the bottom outlet of the catalyst bed layer is connected to the bottom discharge outlet of the plate fixed-bed carbonylation reactor through a pipeline; and at a top of the plate fixed-bed carbonylation reactor, a top feed inlet of the plate fixed-bed carbonylation reactor is connected to the top inlet of the catalyst bed layer through a pipeline, and the top outlet of the plate group fixing chamber is connected to a top coolant outlet of the plate fixed-bed carbonylation reactor through a pipeline.

Preferably, the esterification reaction tower is a packing tower.

Preferably, the esterification reaction tower is a tower plate-packing combined tower having a tower plate portion and a packing packed portion.

Preferably, the methanol washing tower, the methanol rectification tower, the methanol recovery tower, the NO recovery tower, the MN recovery tower, the DMO rectification tower and the nitric acid concentration tower are packing towers, plate towers or bubble towers.

Preferably, packing packed in the packing towers is random packing or high efficiency structured packing; a shape of the random packing is a saddle shape, Raschig ring, Pall ring, wheel ring, intalox saddle ring, spherical shape or columnar shape; and the high efficiency structured packing is corrugated packing, grid packing or impulse packing.

Preferably, the hydrogenation reactor is a plate reactor, a tube reactor or a tube-plate combined reactor.

More preferably, the hydrogenation reactor is a plate fixed-bed hydrogenation reactor.

Preferably, a center of the plate fixed-bed hydrogenation reactor is provided with a plate group fixing chamber, a plate group is provided in the plate group fixing chamber and the plate group fixing chamber is further provided with a bottom inlet and a top outlet; a catalyst bed layer is provided between an outer wall of the plate group fixing chamber and an inner wall of the plate fixed-bed hydrogenation reactor; the catalyst bed layer is packed with a hydrogenation reaction catalyst and the catalyst bed layer is further provided with a top inlet and a bottom outlet; at a bottom of the plate fixed-bed hydrogenation reactor, a bottom coolant inlet of the plate fixed-bed hydrogenation reactor is connected to the bottom inlet of the plate group fixing chamber through a pipeline, and the bottom outlet of the catalyst bed layer is connected to the bottom discharge outlet of the plate fixed-bed hydrogenation reactor through a pipeline; and at a top of the plate fixed-bed hydrogenation reactor, a top feed inlet of the plate fixed-bed hydrogenation reactor is connected to the top inlet of the catalyst bed layer through a pipeline, and the top outlet of the plate group fixing chamber is connected to a top coolant outlet of the plate fixed-bed hydrogenation reactor through a pipeline.

Preferably, the membrane separator consists of 1-100 hollow fiber membrane modules connected in parallel or in series.

A method for producing dimethyl oxalate through high-pressure carbonylation of industrial synthesis gas and producing ethylene glycol through dimethyl oxalate hydrogenation comprises the steps that industrial NO, $O_2$ and methanol are used as raw materials to perform an esterification reaction to produce methyl nitrite, then industrial CO and methyl nitrite are used to perform a carbonylation reaction to produce carbonylation products mainly including dimethyl oxalate and dimethyl carbonate, the carbonylation products are separated to obtain dimethyl carbonate products, dimethyl oxalate is subsequently hydrogenated to produce ethylene glycol products, and waste acid produced during the esterification reaction and purge gas produced during the carbonylation reaction are subjected to coupled recovery treatment for recycling.

Reaction equations are as follows:

Esterification reaction: $4NO+O_2+4CH_3OH \rightarrow 4CH_3ONO+2H_2O$;

Carbonylation reaction: $2CO+2CH_3ONO \rightarrow (COOCH_3)_2+2NO$;

Hydrogenation reaction: $(COOCH_3)_2+4H_2 \rightarrow (CH_2OH)_2+2CH_3OH$;

Overall reaction: $4CO+O_2+8H_2 \rightarrow 2(CH_2OH)_2+2H_2O$.

The method for producing dimethyl oxalate through high-pressure carbonylation of industrial synthesis gas and producing ethylene glycol through dimethyl oxalate hydrogenation specifically comprises the following steps:

(1) industrial NO, $O_2$ and methanol are fed into an esterification reaction tower to perform an esterification reaction; methyl nitrite mixed gas at a tower top of the esterification reaction tower is fed into a carbonylation reactor to perform a carbonylation reaction; a part of acidic alcohol solution at a tower bottom of the esterification reaction tower refluxes to the esterification reaction tower, and a part of the acidic alcohol solution is fed into a methanol recovery tower; a part of methanol recovered at a tower top of the methanol recovery tower is cycled to the esterification reaction tower for recycling, and the other part of the methanol enters an MN recovery tower as washing solution; and waste acid at a tower bottom of the methanol recovery tower enters a nitric acid concentration tower to perform concentration treatment;

(2) the methyl nitrite coming from the esterification reaction tower and industrial CO and $N_2$ feed enter the carbonylation reactor to perform a carbonylation reaction under the existence of a carbonylation reaction catalyst, wherein carbonylation reaction temperature is 30-200° C., reaction pressure is 1-10 MPa and gas hourly space velocity is 3000-30000 h$^{-1}$;

(3) carbonylation products enter a first gas-liquid separator to perform gas-liquid separation, a gas phase enters a methanol washing tower and a liquid phase enters a methanol rectification tower; a part of gas phase components at a tower top of the methanol washing tower is cycled to the esterification reaction tower, and a part of the gas phase components enters an NO recovery tower as purge gas to perform recovery treatment; liquid phase components at a tower bottom of the methanol washing tower enter the methanol rectification tower to perform rectification and separation; methanol and methyl nitrite mixture recovered at a tower top of the methanol rectification tower is cycled to the esterification reaction tower for recycling, and heavy components at a tower bottom enter a DMO rectification tower; and DMC products are obtained at a tower top of the DMO rectification tower, and dimethyl oxalate components at a tower bottom enter a hydrogenation reactor to perform a hydrogenation reaction;

(4) the waste acid coming from the methanol recovery tower is concentrated to nitric acid concentration of 10-68 wt % through the nitric acid concentration tower, and then the concentrated waste acid is cycled to the NO recovery tower; concentrated nitric acid, methanol and purge gas coming from the methanol washing tower experience an esterification regeneration reaction in the NO recovery tower; gas phase light components at a tower top of the NO recovery tower enter the MN recovery tower, and methanol-containing nitric acid waste liquid produced at a tower bottom is cycled to the methanol recovery tower to perform further recovery treatment; gas phase feed obtained after recovered methanol washing in the MN recovery tower enters a pressure swing adsorption tank, and methyl nitrite-containing alcohol solution at a tower bottom of the MN recovery tower enters the esterification reaction tower; and $CO_2$ separated by the pressure swing adsorption tank is exhausted to external for treatment, and recovered $N_2$ and CO purified gas enter the carbonylation reactor for recycling;

(5) the dimethyl oxalate components coming from the DMO rectification tower are mixed with industrial hydrogen pressurized by a hydrogenation recycle compressor, and the mixture enters the hydrogenation reactor, and a hydrogenation reaction is performed under the existence of a hydrogenation catalyst to produce methanol, ethylene glycol, etc., wherein hydrogenation reaction temperature is 160-320° C., reaction pressure is 1-10 MP and liquid hourly space velocity is 1-3 Kg/Kg·h; and (6) hydrogenation products enter a second gas-liquid separator to perform gas-liquid separation, a part of a gas phase is pressurized through the hydrogenation recycle compressor and then is cycled to the hydrogenation rector, the other part of the gas phase enters a membrane separator to perform recovery treatment, and then is returned to the hydrogenation reactor for recycling, while a liquid phase enters an ethylene glycol product tower to perform separation to obtain ethylene glycol products.

Herein, preferably, the carbonylation reactor is externally connected to a dehydration tower; and the gas phase recovered by the pressure swing adsorption tank and the methyl nitrite mixed gas coming from the tower top of the esterification reaction tower are dehydrated by the dehydration tower and then enter the carbonylation reactor to perform the carbonylation reaction.

Preferably, the dehydration tower consists of a molecular sieve dryer A and a molecular sieve dryer B which alternatively run and are regenerated; the molecular sieve dryer A and the molecular sieve dryer B are packed with adsorbents; and the adsorbents are selected from a group consisting of 3 A molecular sieve, 4 A molecular sieve, 5 A molecular sieve, 9 A molecular sieve and calcium oxide. Operating temperature of the molecular sieve dryer A and the molecular sieve dryer B is 40-260° C. and pressure is 1-10 MPa. Unless specially pointed out, pressure in the present invention refers to meter pressure.

Preferably, dried gas is obtained through treatment of the dehydration tower, and a content of water in the dried gas 0.1-100 ppm.

Preferably, the carbonylation reactor is externally connected to an outlet heat exchanger I; and the industrial CO and $N_2$ and dried gas coming from the dehydration tower are used as carbonylation reaction raw materials, exchange heat with the carbonylation reaction products coming from the carbonylation reactor through the outlet heat exchanger I and then enter the carbonylation reactor to perform the carbonylation reaction.

Preferably, the part of gas phase components coming from the tower top of the methanol washing tower is pressurized by a carbonylation recycle compressor and then enters the esterification reaction tower.

Preferably, the gas phase light components at the tower top of the NO recovery tower are compressed and pressurized by a compressor and then enter the MN recovery tower.

Preferably, the hydrogenation reactor is externally connected to an outlet heat exchanger II; and the dimethyl oxalate components coming from the DMO rectification tower, the industrial hydrogen and recycled gas coming from a pressurization recycle compressor and recovered gas coming from the membrane separator are used as hydrogenation reaction raw materials, exchange heat with the hydrogenation products coming from the hydrogenation reactor through the outlet heat exchanger II and then enter the hydrogenation reactor to perform the hydrogenation reaction.

Preferably, a liquid phase separated by the second gas-liquid separator firstly enters a methanol separation tower; non-condensable gas recovered at a tower top of the methanol separation tower enters the membrane separator, a part of liquid phase light components such as methanol recovered at the top of the methanol separation tower enters an upper portion of the methanol washing tower as washing liquid, and the other part enters the NO recovery tower; liquid phase heavy components at a tower bottom of the methanol separation tower enter a light component rectification tower to perform further separation and purification; light components at a tower top of the light component rectification tower enter an external alcohol recovery device to perform recovery treatment; heavy components at a tower bottom of the light component rectification tower enter the ethylene glycol product tower; and light components at a tower top of the ethylene glycol product tower enter an external 1,2-BDO recovery treatment device to perform further recovery treatment, heavy components at a tower bottom of the ethylene glycol product tower enter an external recovery treatment device to perform subsequent treatment, and ethylene glycol products are introduced out from an upper side line of the ethylene glycol product tower.

Preferably, the second gas-liquid separator comprises a high-pressure gas-liquid separator and a low-pressure gas-liquid separator; a part of a gas phase separated by the high-pressure gas-liquid separator enters the hydrogenation recycle compressor and the other part enters the low-pressure gas-liquid separator; a liquid phase separated by the high-pressure gas-liquid separator enters the methanol separation tower; and a gas phase separated by the low-pressure gas-liquid separator enters the membrane separator, and a liquid phase separated by the low-pressure gas-liquid separator enters the methanol separation tower.

Preferably, 0.1-10 v % of the gas phase separated by the high-pressure gas-liquid separator enters the low-pressure gas-liquid separator.

Preferably, the gas phase separated by the low-pressure gas-liquid separator and the non-condensable gas coming from the methanol separation tower enter the membrane separator after methanol is absorbed by a methanol absorption tank.

Preferably, the carbonylation reactor is a plate reactor, a tube reactor or a tube-plate combined reactor.

More preferably, the carbonylation reactor is a plate fixed-bed carbonylation reactor.

Preferably, a center of the plate fixed-bed carbonylation reactor is provided with a plate group fixing chamber, and a plate group is provided in the plate group fixing chamber; a catalyst bed layer is provided between an outer wall of the plate group fixing chamber and an inner wall of the plate fixed-bed carbonylation reactor; the catalyst bed layer is packed with a carbonylation reaction catalyst; after temperature of carbonylation reaction raw materials reaches inlet temperature of the catalyst bed layer, the carbonylation reaction raw materials enter the catalyst bed layer from a top of the plate fixed-bed carbonylation reactor to perform a carbonylation reaction; coolants introduced inside from the outside enter the plate group fixing chamber from a bottom of the plate fixed-bed carbonylation reactor and are introduced outside from the top of the plate fixed-bed carbonylation reactor, and heat exchange is performed in a backflow method to take away reaction heat produced during the carbonylation reaction; and carbonylation products coming from a bottom of the catalyst bed layer are introduced outside from the bottom of the plate fixed-bed carbonylation reactor.

Preferably, the plate fixed-bed carbonylation reactor is externally connected to a steam drum I; coolants introduced inside from the outside enter the steam drum I, and the coolants in the steam drum I enter the plate group fixing chamber of the plate fixed-bed carbonylation reactor and exchange heat with the catalyst bed layer to remove reaction heat; and the heated coolants are steam-liquid mixture and enter the steam drum I to perform gas-liquid separation, and produced low-pressure saturated steam enters an external low-pressure steam recovery system for recycling.

Preferably, the carbonylation reaction catalyst is a commercially available catalyst produced by Shanghai Wuzheng Engineering Technology Co., Ltd., and an product model of the catalyst is DMO-0701T.

Preferably, the esterification reaction tower is a packing tower.

Preferably, the esterification reaction tower is a tower plate-packing combined tower having a tower plate portion and a packing packed portion.

Preferably, a theoretical plate number of the esterification reaction tower is 20-50. Serial numbers of tower plates of all towers are expressed in sequence, a tower plate at a tower top is referred as a first tower plate, and then the tower plates are arranged from the tower top to the tower bottom according to the serial numbers.

Preferably, in the feed of the esterification reaction tower, the $O_2$ is respectively fed from 16th-50th tower plates in 2-8 loops; the NO and the gas phase light components coming from the tower top of the methanol washing tower are fed from 18th-50th tower plates; the fresh methanol, the recovered methanol coming from the tower top of the methanol recovery tower, the recovered methanol and methyl nitrite mixture coming from the tower top of the methanol rectification tower and the methyl nitrite-containing alcohol solution coming from the tower bottom of the MN recovery tower are fed from 1st-5th tower plates; reflux materials from the tower bottom of the esterification reaction tower are fed from 10th-25th tower plates.

Preferably, a molar ratio of $O_2$ to NO to methanol in the esterification reaction tower is (0.01-0.8):(0.1-3.2):(0.8-50).

Preferably, tower top temperature of the esterification reaction tower is 30-80° C., tower bottom temperature is 50-200° C., reaction area temperature is 50-160° C. and reaction pressure is 0.5-10 MPa.

Preferably, the methanol recovery tower, the methanol washing tower, the methanol rectification tower, the nitric acid concentration tower, the NO recovery tower, the MN recovery tower and the DMO rectification tower are packing towers, plate towers or bubble towers.

Preferably, packing packed in the packing towers is random packing or high efficiency structured packing; a shape of the random packing is a saddle shape, Raschig ring, Pall ring, wheel ring, intalox saddle ring, spherical shape or columnar shape; and the high efficiency structured packing is corrugated packing, grid packing or impulse packing.

Preferably, a theoretical tower plate number of the methanol recovery tower is 5-50, tower top temperature is 40-150° C., tower bottom temperature is 60-230° C. and tower top pressure is 0.01-2.0 MPa.

Preferably, a reflux ratio of the light components at the tower top of the methanol recovery tower is 0.1-3.0.

Preferably, a proportion of the part, which cyclically enters the esterification reaction tower, in the recovered methanol at the tower top of the methanol recovery tower is 10-90 wt %.

Preferably, a theoretical tower plate number of the methanol washing tower is 10-50, tower top temperature is 15-70° C., tower bottom temperature is 10-100° C. and tower top pressure is 0.9-10 MPa.

Preferably, a proportion of the purge gas in the gas phase components at the tower top of the methanol washing tower is 0.05-5 v %.

Preferably, the methanol rectification tower is an extraction rectification tower, a theoretical tower plate number is 10-60, tower top temperature is 50-150° C., tower bottom temperature is 130-250° C. and tower top pressure is 0.01-0.5 MPa.

Preferably, a theoretical tower plate number of the nitric acid concentration tower is 1-30, tower top temperature is 30-110° C., tower bottom temperature is 60-160° C. and tower top pressure is 0.01-0.3 MPa.

Preferably, a reflux ratio of the light components at the tower top of the nitric acid concentration tower is 0.01-3.

Preferably, a theoretical tower plate number of the NO recovery tower is 5-30, tower top temperature is 30-120° C., tower bottom temperature is 50-200° C. and tower top pressure is 1-10 MPa.

Preferably, the purge gas is fed from 5th-30th tower plates of the NO recovery tower; the concentrated nitric acid is fed from 1st-10th tower plates of the NO recovery tower; and the recovered methanol coming from the tower top of the methanol separation tower is fed from 1st-10th tower plates.

Preferably, a molar ratio of nitric acid to methanol to NO in purge gas in the NO recovery tower is (1.1-10):(2-100):(1-5).

Preferably, a theoretical tower plate number of the MN recovery tower is 10-60, tower top temperature is 0-50° C., tower bottom temperature is 0-80° C. and reaction pressure is 1-10 MPa.

Preferably, a theoretical tower plate number of the DMO rectification tower is 10-50, tower top temperature is 80-120° C., tower bottom temperature is 120-200° C. and operation is performed at normal pressure or reduced pressure.

Preferably, a reflux ratio of the light components at the tower top of the DMO rectification tower is 0.1-100.

Preferably, components of purified gas recovered in the pressure swing adsorption tank comprise 60-80 v % of $N_2$ and 20-40 v % of CO; and separated $CO_2$ gas accounts for 0.1-5 v % of total amount of inlet gas, wherein a concentration of $CO_2$ is 99.8-99.9 v %; and the separated $CO_2$ gas may be treated through an external device.

Preferably, the hydrogenation reactor is a plate reactor, a tube reactor or a tube-plate combined reactor.

More preferably, the hydrogenation reactor is a plate fixed-bed hydrogenation reactor.

Preferably, a center of the plate fixed-bed hydrogenation reactor is provided with a plate group fixing chamber, and a plate group is provided in the plate group fixing chamber; a catalyst bed layer is provided between an outer wall of the plate group fixing chamber and an inner wall of the plate fixed-bed hydrogenation reactor; the catalyst bed layer is packed with a hydrogenation reaction catalyst; after temperature of hydrogenation reaction raw materials reaches inlet temperature of the catalyst bed layer, the hydrogenation reaction raw materials enter the catalyst bed layer from a top of the plate fixed-bed hydrogenation reactor to perform a hydrogenation reaction; coolants introduced inside from the outside enter the plate group fixing chamber from a bottom of the plate fixed-bed hydrogenation reactor and are introduced outside from the top of the plate fixed-bed hydrogenation reactor, and heat exchange is performed in a backflow method to take away reaction heat produced during the hydrogenation reaction; and hydrogenation products coming from a bottom of the catalyst bed layer are introduced outside from the bottom of the plate fixed-bed hydrogenation reactor.

Preferably, the plate fixed-bed hydrogenation reactor is externally connected to a steam drum II; coolants introduced inside from the outside enter the steam drum II, and the coolants in the steam drum II enter the plate group fixing chamber of the plate fixed-bed hydrogenation reactor and exchange heat with the catalyst bed layer to remove reaction heat; and the heated coolants are steam-liquid mixture and enter the steam drum II to perform gas-liquid separation, and produced low-pressure saturated steam enters the external low-pressure steam recovery system for recycling.

Preferably, the coolants are water or heat conducting oil, and are preferably water.

Preferably, the plate fixed-bed hydrogenation reactor is externally connected to a startup heater; at an initial stage of startup, temperature does not satisfy a reaction requirement, hydrogenation reaction raw materials enter the startup heater to perform preheating, and after the inlet temperature of the catalyst bed layer is reached through preheating, the hydrogenation reaction raw materials enter the catalyst bed layer to perform a hydrogenation reaction; at the initial stage of startup, the startup heater provides a unique heat source for the hydrogenation reaction in the plate fixed-bed hydrogenation reactor; and a heat source of the startup heater is low-pressure steam.

Preferably, the hydrogenation reaction catalyst is a commercially available catalyst produced by Shanghai Wuzheng Engineering Technology Co., Ltd., and an product model of the catalyst is MEG-801T.

Preferably, a theoretical tower plate number of the methanol separation tower is 10-40, tower top temperature is 40-70° C., tower bottom temperature is 80-180° C. and operation is performed at normal pressure or reduced pressure; and a reflux ratio of the light components at the tower top of the methanol separation tower is 0.1-3.

Preferably, a theoretical tower plate number of the light component rectification tower is 10-60, tower top temperature is 58-90° C., tower bottom temperature is 70-160° C. and tower top absolute pressure is 5-50 KPa.

Preferably, a reflux ratio of the light components at the tower top of the light component rectification tower is 1-50.

Preferably, a theoretical tower plate number of the ethylene glycol product tower is 30-100, tower top temperature is 100-150° C., tower bottom temperature is 130-230° C. and tower top absolute pressure is 5-50 KPa; and a reflux ratio of the light components at the tower top of the ethylene glycol product tower is 50-200 or total reflux.

Preferably, the membrane separator consists of 1-100 hollow fiber membrane modules connected in parallel or in series.

Preferably, tolerable pressure of a tube shell of the membrane separator is 4.75 MPa, and a maximum pressure difference is 1.5 MPa (raw material gas to permeable gas); and the highest operating temperature of the membrane separator is 85° C.

Preferably, a concentration of hydrogen in purified gas obtained through separation and purification performed by the membrane separator is 88-99.00 v % and a hydrogen recovery rate is 90-98.5%.

A basic principle of the membrane separator is that, a partial pressure difference between gases on two sides of a hollow fiber membrane is used as a driving force, and a purpose of separation is achieved through steps such as permeation-dissolution-diffusion-desorption by using the feature that selective permeability of the hollow fiber membrane to each kind of gas is different. Raw material gas goes through a shell pass of a hollow fiber membrane module, permeable gas goes through a tube pass, and tail gas enters a next hollow fiber membrane module. Since a permeation rate of $H_2$ on a surface of the membrane is tens of times of that of $CH_4$, $N_2$, Ar, etc., after $H_2$ enters each hollow fiber tube and is gathered, $H_2$ is exhausted from the lower portion of the membrane separator and impermeable gas (tail gas) is exhausted from the upper portion of the hollow fiber membrane module. An interior portion of the hollow fiber membrane module is a core consisting of 1000-100000 hollow fiber membrane filament tubes, and fiber tubes are manufactured by using high-molecular materials through special processing. Raw material gas enters from a side opening of the separator, gas is subjected to dissolution, permeation and diffusion processes on fiber walls when gas which flows downwards along outer sides of fiber tube bundles is in contact with outer surfaces of fiber membrane filament tubes, and different types of gases are separated by using differences in dissolution and permeation capacities of different gases.

The present invention has the following technical effects and advantages:

Since high-pressure operation is adopted in the carbonylation system and the esterification system, the equipment volume requirement of the large-size process device for producing ethylene glycol through synthesis gas can be greatly reduced, the production enlargement of the single-series device is facilitated, the safety production of the device is facilitated and the equipment investment is decreased.

Since a nitric acid waste liquid recycling method and a purge gas recycling method a highly coupled, waste liquid produced in the device can be cyclically treated and used as a raw material for recovering purge gas containing a great amount of carbon monoxide to produce methyl nitrite which is needed for the main reaction. The method combined technology is scientific and reasonable, the full recycling of discharged waste gas and waste liquid is realized through one reactor, and it is economic and environmental-friendly.

The methyl nitrite is a thermally sensitive substance, the decomposition of the methyl nitrite is continuously intensified with the continuous increase of temperature especially after the temperature is higher than certain temperature, the reaction for producing dimethyl oxalate through CO carbonylation coupling is a strong exothermic reaction, and thus adopting a suitable reactor to keep uniform temperature distribution of the bed layer and control reaction hotspot temperature is a key to prevent methyl nitrite from being decomposed and improve the yield of products. The carbonylation plate reactor in the present invention is a plate reactor and realizes the reaction for producing dimethyl oxalate through CO carbonylation coupling, the feature of uniform temperature distribution of the reactor can be fully utilized and thereby the features of improving the space-time yield of dimethyl oxalate and recycling reaction heat are achieved. At the same time, the utilization coefficient of the catalyst and the volume utilization ratio of the reactor are improved, the packing capacity of the catalyst is increased and the production capacity of the reactor is improved. Such reaction feature can also obtain the same energy saving and consumption reduction effects in the production of ethylene glycol through dimethyl oxalate hydrogenation.

By recovering the purge gas at the hydrogenation section of the method, the precious hydrogen resource is fully saved, the unit coal consumption is reduced, the overall energy consumption and pollutant discharge of the device are reduced and it has a relatively realistic significance. Moreover, for the membrane separation system adopted for recovering the purge gas at the hydrogenation section of the method, the reaction system pressure under the equivalent load can be reduced by about 1 MPa, and for the compression system, the decrease of the outlet pressure can greatly reduce power consumption. The precious hydrogen resource is fully saved, the unit coal consumption is reduced, the overall energy consumption and pollutant discharge of the device are reduced, and it has a relatively realistic significance. By adopting the membrane separation system, the hydrogenation reaction speed is improved and the daily output of ethylene glycol is increased by about 10% relative to the traditional method.

To sum up, by adopting the high-pressure method flow and the plate reactor, the device enlargement bottleneck is effectively solved, the equipment investment is reduced, effective heat recovery is realized by recovering the reaction waste heat, the unit energy consumption for ethylene glycol production is reduced, the consumption of steam and cooling water is reduced; and by coupling waste gas and waste liquid processes, the discharged toxins are reduced and the dual purposes of energy saving and environmental protection are achieved. The present invention realizes the full reuse of the discharged waste gas and waste liquid and the comprehensive energy utilization of the reaction heat of the device and the heat separated from the towers, the energy utilization efficiency is improved, the energy consumption is reduced and the industrial application value is remarkable. The present invention provides a guarantee for the development of the technology for producing ethylene glycol through synthesis gas towards a more environmental-friendly, higher-efficiency and more energy-saving technology. By adopting the present invention, it is technically feasible and economically reasonable.

The above-mentioned method optimization design can remarkably improve the yield and has not been ever recorded in any literature. To view from the angle of energy consumption, the method provided by the present invention is also particularly beneficial, has the feature of remarkably reducing energy consumption, and achieves a very remarkable effect by jointly adopting useful substance recycling steps, especially through the high coupling of the nitric acid waste liquid recycling method and the purge gas recycling method, the separation method thereof and the recycling and recovery of hydrogen in the waste gas produced in reaction.

DESCRIPTION OF COMPONENT MARK NUMBERS

1: carbonylation reactor; 2: steam drum I; 3: outlet heat exchanger I; 4: first gas-liquid separator; 5: methanol rectification tower; 6: DMO rectification tower; 7: methanol washing tower; 8: carbonylation recycle compressor; 9: esterification reaction tower; 10: dehydration tower; 11: methanol recovery tower; 12: nitric acid concentration tower; 13: NO recovery tower; 14: compressor; 15: MN recovery tower; 16: pressure swing absorption tank; 17: hydrogenation reactor; 18: steam drum II; 19: startup heater; 20: outlet heat exchanger II; 21: high-pressure gas-liquid separator; 22: methanol separation tower; 23: light component rectification tower; 24: ethylene glycol product tower; 25: hydrogenation recycle compressor; 26: low-pressure gas-liquid separator; 27: methanol absorption tank; 28: membrane separator.

DETAILED DESCRIPTION OF THE PREFERRED EMBODIMENTS

The technical solution of the present invention will be described below through specific embodiments. It should be understood that one or more method steps mentioned in the present invention do not exclude the situation that there are other method steps before and after the steps or other method steps may be inserted between these clearly mentioned steps; and it also should be understood that these embodiments are just used for describing the present invention instead of limiting the scope of the present invention. In addition, unless otherwise stated, serial numbers of all method steps are just convenient tools for distinguishing the method steps instead of limiting the arrangement sequence of the method steps or limiting the implementable scope of the present invention, and variation or adjustment of relative relationships therebetween shall be still viewed as the implementable scope of the present invention under the situation that the technical contents are not substantively changed.

Experiment methods for which specific conditions are not clearly noted in the embodiments below are usually performed according to conventional conditions, e.g., conditions recommended in chemical operation manuals or by manufacturers.

Figure 1:
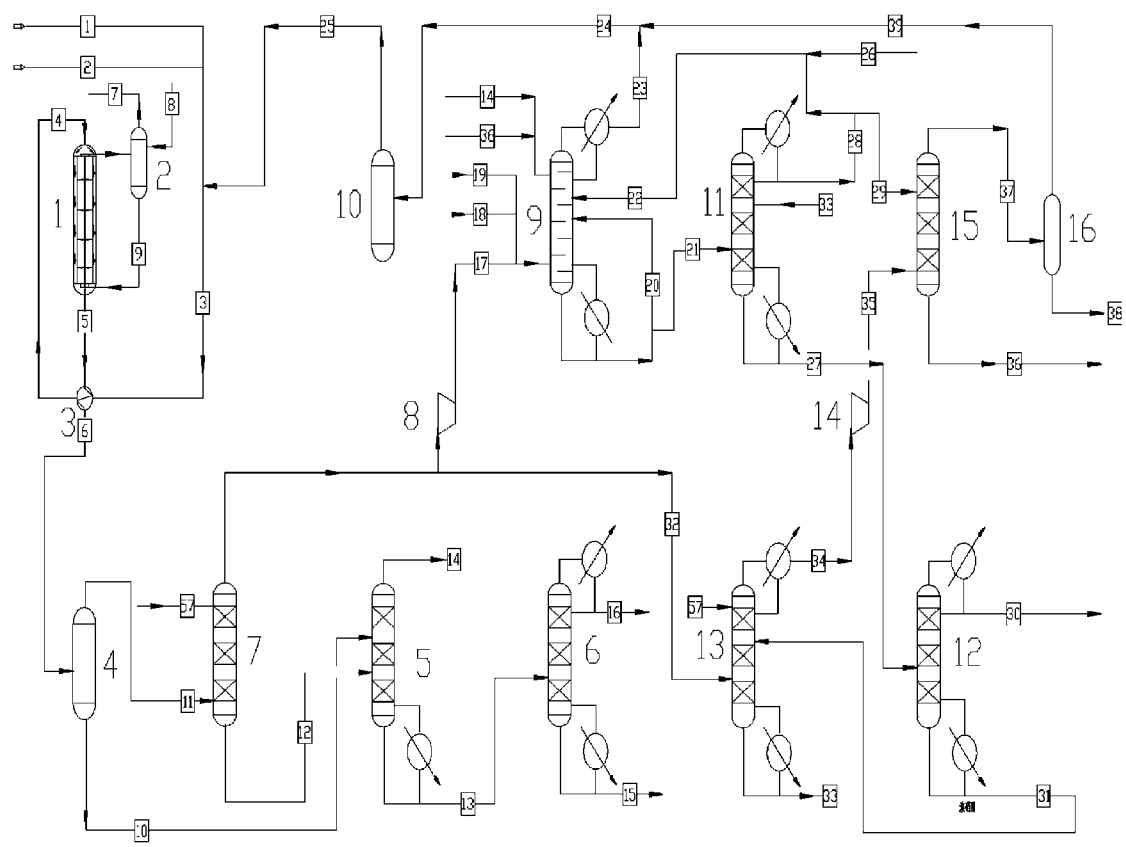
FIG. 1 illustrates a device system (part) for producing dimethyl oxalate through high-pressure carbonylation of industrial synthesis gas and producing ethylene glycol through dimethyl oxalate hydrogenation.
Figure 2:
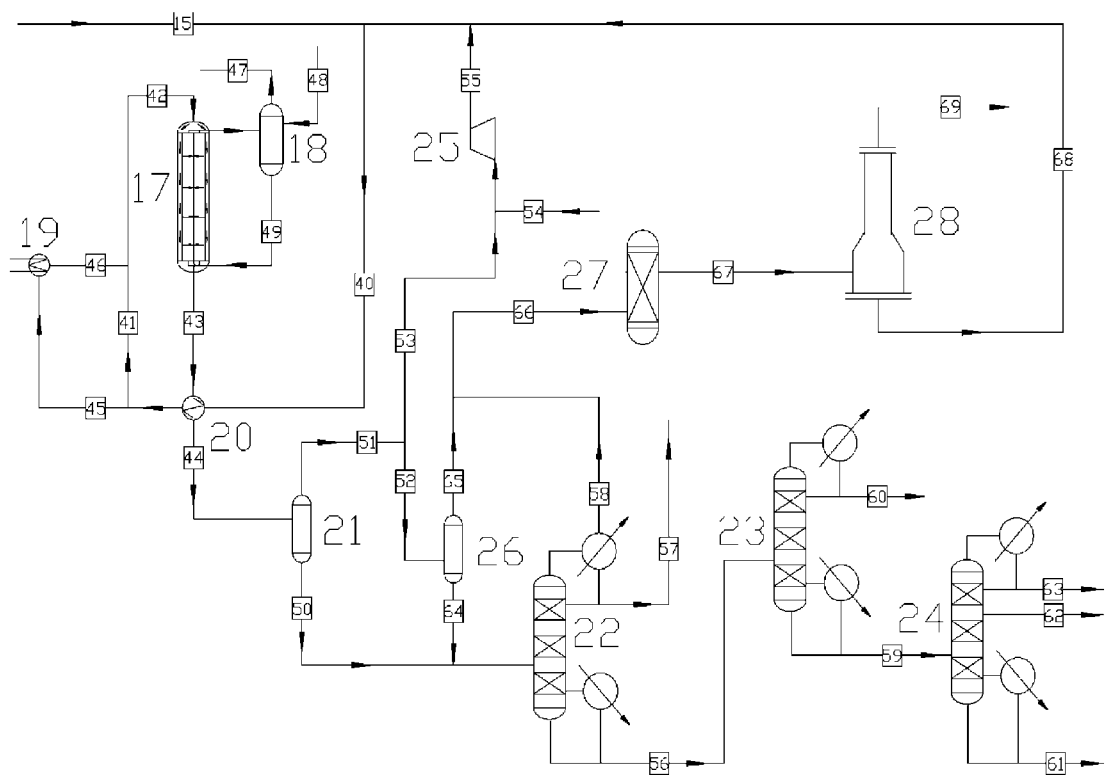
FIG. 2 illustrates a device system (part) for producing dimethyl oxalate through high-pressure carbonylation of industrial synthesis gas and producing ethylene glycol through dimethyl oxalate hydrogenation.

As illustrated in FIG. 1 and FIG. 2, a device system for producing dimethyl oxalate through high-pressure carbonylation of industrial synthesis gas and producing ethylene glycol through dimethyl oxalate hydrogenation comprises a carbonylation reaction system, an esterification reaction system, a purge gas and waste acid coupled recovery system and a hydrogenation reaction system;

the carbonylation reaction system comprises a carbonylation reactor 1, a first gas-liquid separator 4, a methanol washing tower 7, a methanol rectification tower 5 and a DMO rectification tower 6; the carbonylation reactor 1 is provided with a top feed inlet, a bottom discharge outlet, a bottom coolant inlet and a top coolant outlet; the first gas-liquid separator 4 is provided with a feed inlet, a gas outlet and a liquid outlet; the methanol washing tower 7 is provided with an upper feed inlet, a lower feed inlet, a top outlet and a bottom outlet; the methanol rectification tower 5 is provided with an upper feed inlet, a lower feed inlet, a top outlet and a bottom outlet; the DMO rectification tower 6 is provided with a lower feed inlet, a top outlet and a bottom outlet;

the esterification reaction system comprises an esterification reaction tower 9 and a methanol recovery tower 11; the esterification reaction tower 9 is provided with a top feed inlet, an upper feed inlet, a plurality of lower feed inlets, a middle reflux inlet, a top outlet and a bottom outlet; the methanol recovery tower 11 is provided with a middle-lower feed inlet, a lower feed inlet, a top outlet and a bottom outlet;

the purge gas and waste acid coupled recovery system comprises a nitric acid concentration tower 12, an NO recovery tower 13, an MN recovery tower 15 and a pressure swing adsorption tank 16; the nitric acid concentration tower 12 is provided with a middle feed inlet, a top outlet and a bottom outlet; the NO recovery tower 13 is provided with a top feed inlet, a middle feed inlet, a bottom feed inlet, a top outlet and a bottom outlet; the MN recovery tower 15 is provided with an upper feed inlet, a lower feed inlet, a top outlet and a bottom outlet; the pressure swing adsorption tank 16 is provided with a feed inlet, a recovered gas outlet and an exhaust gas outlet;

the hydrogenation reaction system comprises a hydrogenation recycle compressor 14, a hydrogenation reactor 17, a second gas-liquid separator, a membrane separator 28, a methanol separation tower 22, a light component rectification tower 23 and an ethylene glycol product tower 24; the hydrogenation recycle compressor 14 comprises an inlet and an outlet; the hydrogenation reactor 17 is provided with a top feed inlet, a bottom discharge outlet, a bottom coolant inlet and a top coolant outlet; the second gas-liquid separator is provided with a feed inlet, a gas outlet and a liquid outlet; the membrane separator 28 is provided with a feed inlet, a recovered gas outlet and an exhaust gas outlet; the methanol separation tower 22 is provided with a middle feed inlet, a top non-condensable gas outlet, a top liquid phase light component outlet and a bottom liquid phase heavy component outlet; the light component rectification tower 23 is provided with a lower feed inlet, a top outlet and a bottom outlet; the ethylene glycol product tower 24 is provided with a lower feed inlet, a top outlet, an upper outlet and a bottom outlet;

the top feed inlet of the carbonylation reactor 1 is connected to a CO raw material pipe and an $N_2$ raw material pipe through a pipeline; the bottom discharge outlet of the carbonylation reactor 1 is connected to the feed inlet of the first gas-liquid separator 4 through a pipeline; the gas outlet of the first gas-liquid separator 4 is connected to the lower feed inlet of the methanol washing tower 7 through a pipeline; the liquid outlet of the first gas-liquid separator 4 is connected to the upper feed inlet of the methanol rectification tower 5 through a pipeline; the top outlet of the methanol washing tower 7 is provided with a branch outlet A and a branch outlet B, the branch outlet A is connected to one lower feed inlet of the esterification reaction tower 9 through a pipeline, and the branch outlet B is connected to the bottom feed inlet of the NO recovery tower 13 through a pipeline; the bottom outlet of the methanol washing tower 7 is connected to the lower feed inlet of the methanol rectification tower 5 through a pipeline; the top outlet of the methanol rectification tower 5 is connected to the upper feed inlet of the esterification reaction tower 9 through a pipeline; the bottom outlet of the methanol rectification tower 5 is connected to the lower feed inlet of the DMO rectification tower 6 through a pipeline; the bottom outlet of the DMO rectification tower 6 is connected to the top feed inlet of the hydrogenation reactor 17 through a pipeline, and the top outlet of the DMO rectification tower 6 is a DMC product outlet;

the other lower feed inlets of the esterification reaction tower 9 are respectively connected to an NO raw material pipe and a plurality of $O_2$ raw material pipes through pipelines; the top feed inlet of the esterification reaction tower 9 is connected to a methanol raw material pipe through a pipeline; the bottom outlet of the esterification reaction tower 9 is provided with a branch outlet C and a branch outlet D, the branch outlet C is connected to the middle reflux inlet of the esterification reaction tower 9 through a pipeline, and the branch outlet D is connected to the lower feed inlet of the methanol recovery tower 11 through a pipeline; the top outlet of the esterification reaction tower 9 is connected to the top feed inlet of the carbonylation reactor 1 through a pipeline; the top outlet of the methanol recovery tower 11 is provided with a branch outlet E and a branch outlet F, the branch outlet E is connected to the upper feed inlet of the esterification reaction tower 9 through a pipeline, and the branch outlet F is connected to the upper feed inlet of the MN recovery tower 15 through a pipeline; the bottom outlet of the methanol recovery tower 11 is connected to the middle feed inlet of the nitric acid concentration tower 12 through a pipeline;

the top outlet of the nitric acid concentration tower 12 is a waste liquid drain outlet; the bottom outlet of the nitric acid concentration tower 12 is connected to the middle feed inlet of the NO recovery tower 13 through a pipeline; the top outlet of the NO recovery tower 13 is connected to the lower feed inlet of the MN recovery tower 15 through a pipeline; the bottom outlet of the NO recovery tower 13 is connected to the middle-lower feed inlet of the methanol recovery tower 11 through a pipeline; the top outlet of the MN recovery tower 15 is connected to the feed inlet of the pressure swing adsorption tank 16 through a pipeline; the bottom outlet of the MN recovery tower 15 is connected with the upper feed inlet of the esterification reaction tower 9 through a pipeline; the recovered gas outlet of the pressure swing adsorption tank 16 is connected to the top feed inlet of the carbonylation reactor 1 through a pipeline; the exhaust gas outlet of the pressure swing adsorption tank 16 is connected to an external recovery device through a pipeline;

the inlet of the hydrogenation recycle compressor 14 is connected to an industrial hydrogen raw material pipe through a pipeline, and the outlet of the hydrogenation recycle compressor 14 is connected to the top feed inlet of the hydrogenation reactor 17 through a pipeline; the bottom discharge outlet of the hydrogenation reactor 17 is connected to the feed inlet of the second gas-liquid separator through a pipeline; the gas outlet of the second gas-liquid separator is provided with a branch outlet G and a branch outlet H, the branch outlet G is connected to the inlet of the hydrogenation recycle compressor 14 through a pipeline, and the branch outlet H is connected to the feed inlet of the membrane separator 28 through a pipeline; the liquid outlet of the second gas-liquid separator is connected to the lower feed inlet of the methanol separation tower 22 through a pipeline; the top non-condensable gas outlet of the methanol separation tower 22 is connected to the feed inlet of the membrane separator 28 through a pipeline; the top liquid phase light component outlet of the methanol separation tower 22 is provided with a branch outlet I and a branch outlet J, the branch outlet I is connected to the upper feed inlet of the methanol washing tower 7 through a pipeline, and the branch outlet J is connected to the top feed inlet of the NO recovery tower 13 through a pipeline; the bottom liquid phase heavy component outlet of the methanol separation tower 22 is connected to the lower feed inlet of the light component rectification tower 23 through a pipeline; the top light component outlet of the light component rectification tower 23 is connected to an external methanol recovery device through a pipeline; the bottom heavy component outlet of the light component rectification tower 23 is connected to the lower feed inlet of the ethylene glycol product tower 24 through a pipeline; the top outlet of the ethylene glycol product tower 24 is connected to an external 1,2-BDO recovery treatment device through a pipeline; the bottom outlet of the ethylene glycol product tower 24 is connected to an external recovery treatment device through a pipeline; the upper outlet of the ethylene glycol product tower 24 is an ethylene glycol product outlet; and the exhaust gas outlet of the membrane separator 28 is connected to an external recovery device through a pipeline, and the recovered gas outlet of the membrane separator 28 is connected to the top feed inlet of the hydrogenation reactor 17 through a pipeline.

As a preferred embodiment, the carbonylation reactor 1 is externally connected to a dehydration tower 10; the dehydration tower 10 is provided with a feed inlet and a dried gas outlet; the top outlet of the esterification reaction tower 9 and the recovered gas outlet of the pressure swing adsorption tank 16 are connected to the feed inlet of the dehydration tower 10 through pipelines; and the dried gas outlet of the dehydration tower 10 is connected to the top feed inlet of the carbonylation reactor 1 through a pipeline.

The dehydration tower consists of a molecular sieve dryer A and a molecular sieve dryer B which alternatively run and are regenerated; and the molecular sieve dryer A and the molecular sieve dryer B are packed with adsorbents.

As a preferred implementation mode, the bottom discharge outlet of the carbonylation reactor 1 is connected to an outlet heat exchanger I 3; the outlet heat exchanger I 3 is provided with a cold material flow inlet, a cold material flow outlet, a hot material flow inlet and a hot material flow outlet; the CO raw material pipe, the $N_2$ raw material pipe and the dried gas outlet of the dehydration tower 10 are connected to the cold material flow inlet of the outlet heat exchanger I 3 through pipelines; the cold material flow outlet of the outlet heat exchanger I 3 is connected to the top feed inlet of the carbonylation reactor 1 through a pipeline; the bottom discharge outlet of the carbonylation reactor 1 is connected to the hot material flow inlet of the outlet heat exchanger I 3; and the hot material flow outlet of the outlet heat exchanger I 3 is connected to the feed inlet of the first gas-liquid separator 4 through a pipeline.

As a preferred embodiment, the carbonylation reactor 1 is externally connected to a steam drum I 2; the steam drum I 2 is provided with a coolant inlet, a coolant outlet, a steam-liquid mixture inlet and a steam outlet; the coolant inlet of the steam drum I 2 is connected to a coolant raw material pipe through a pipeline; the coolant outlet of the steam drum I 2 is connected to the bottom coolant inlet of the carbonylation plate reactor 1 through a pipeline; the top coolant outlet of the carbonylation reactor 1 is connected to the steam-liquid mixture inlet of the steam drum I 2 through a pipeline; and the steam outlet of the steam drum I 2 is connected to an external steam recovery system through a pipeline.

As a preferred embodiment, a carbonylation recycle compressor 8 is connected between the branch outlet A of the methanol washing tower 7 and the lower feed inlet of the esterification reaction tower 9; the carbonylation recycle compressor 8 is provided with an inlet and an outlet; the branch outlet A is connected to the inlet of the carbonylation recycle compressor 8 through a pipeline; and the outlet of the carbonylation recycle compressor 8 is connected to the lower feed inlet of the esterification reaction tower 9 through a pipeline.

As a preferred embodiment, a compressor 14 is connected between the top outlet of the NO recovery tower 13 and the bottom feed inlet of the MN recovery tower 15; the compressor 14 is provided with an inlet and an outlet; the top outlet of the NO recovery tower 13 is connected to the inlet of the compressor 14 through a pipeline; and the outlet of the compressor is connected to the bottom feed inlet of the MN recovery tower 15 through a pipeline.

As a preferred implementation mode, the bottom discharge outlet of the hydrogenation rector 17 is connected to an outlet heat exchanger II 20; the outlet heat exchanger II 20 is provided with a cold material flow inlet, a cold material flow outlet, a hot material flow inlet and a hot material flow outlet; the bottom outlet of the DMO rectification tower 6, the recovered gas outlet of the membrane separator 28 and the outlet of the hydrogenation recycle compressor 25 are connected to the cold material flow inlet of the outlet heat exchanger II 20 through pipelines; the cold material flow outlet of the outlet heat exchanger II 20 is connected to the top feed inlet of the hydrogenation reactor 17 through a pipeline; the bottom discharge outlet of the hydrogenation reactor 17 is connected to the hot material flow inlet of the outlet heat exchanger II 20 through a pipeline; and the hot material flow outlet of the outlet heat exchanger II 20 is connected to the feed inlet of the second gas-liquid separator through a pipeline.

As a preferred embodiment, the top feed inlet of the hydrogenation reactor 17 is connected to a startup heater 19; the startup heater 19 is provided with a feed inlet and a discharge outlet; the cold material flow outlet of the outlet heat exchanger II 20 is connected to the feed inlet of the startup heater 19 through a pipeline; and the discharge outlet of the startup heater is connected to the top feed inlet of the hydrogenation reactor 17 through a pipeline.

As a preferred embodiment, the hydrogenation reactor 17 is externally connected to a steam drum II 18; the steam drum II 18 is provided with a coolant inlet, a coolant outlet, a steam-liquid mixture inlet and a steam outlet; the coolant inlet of the steam drum II 18 is connected to a coolant raw material pipe through a pipeline; the coolant outlet of the steam drum II 18 is connected to the bottom coolant inlet of the hydrogenation reactor 17 through a pipeline; the top coolant outlet of the hydrogenation reactor 17 is connected to the steam-liquid mixture inlet of the steam drum II 18 through a pipeline; and the steam outlet of the steam drum II 18 is connected to an external steam recovery system through a pipeline.

As a preferred embodiment, the second gas-liquid separator comprises a high-pressure gas-liquid separator 21 and a low-pressure gas-liquid separator 26; the high-pressure gas-liquid separator 21 is provided with a feed inlet, a gas outlet and a liquid outlet; the low-pressure gas-liquid separator 26 is provided with a feed inlet, a gas outlet and a liquid outlet; the bottom discharge outlet of the hydrogenation reactor 17 is connected to the feed inlet of the high-pressure gas-liquid separator 21 through a pipeline; the gas outlet of the high-pressure gas-liquid separator 21 is provided with a branch outlet K and a branch outlet L, the branch outlet K is connected to the inlet of the hydrogenation recycle compressor 25 through a pipeline, and the branch outlet L is connected to the feed inlet of the low-pressure gas-liquid separator 26 through a pipeline; the liquid outlet of the high-pressure gas-liquid separator 21 is connected to the middle feed inlet of the methanol separation tower 22 through a pipeline; the gas outlet of the low-pressure gas-liquid separator 26 is connected to the feed inlet of the membrane separator 28 through a pipeline; and the liquid outlet of the low-pressure gas-liquid separator 26 is connected to the middle feed inlet of the methanol separation tower 22 through a pipeline.

As a preferred embodiment, a methanol absorption tank 27 is provided in front of the feed inlet of the membrane separator 28; the methanol absorption tank 27 is provided with a feed inlet and a purified gas outlet; the gas outlet of the low-pressure gas-liquid separator 26 and the top non-condensable gas outlet of the methanol separation tower 22 are connected to the feed inlet of the methanol absorption tank 27 through pipelines; and the purified gas outlet of the methanol absorption tank 27 is connected to the feed inlet of the membrane separator 28 through a pipeline.

The carbonylation reactor 1 is a plate reactor, a tube reactor or a tube-plate combined reactor.

As a preferred embodiment, the carbonylation reactor 1 is a plate fixed-bed carbonylation reactor;

a center of the plate fixed-bed carbonylation reactor is provided with a plate group fixing chamber, a plate group is provided in the plate group fixing chamber and the plate group fixing chamber is further provided with a bottom inlet and a top outlet; a catalyst bed layer is provided between an outer wall of the plate group fixing chamber and an inner wall of the plate fixed-bed carbonylation reactor; the catalyst bed layer is packed with a carbonylation reaction catalyst and the catalyst bed layer is further provided with a top inlet and a bottom outlet; at a bottom of the plate fixed-bed carbonylation reactor, a bottom coolant inlet of the plate fixed-bed carbonylation reactor is connected to the bottom inlet of the plate group fixing chamber through a pipeline, and the bottom outlet of the catalyst bed layer is connected to the bottom discharge outlet of the plate fixed-bed carbonylation reactor through a pipeline; and at a top of the plate fixed-bed carbonylation reactor, a top feed inlet of the plate fixed-bed carbonylation reactor is connected to the top inlet of the catalyst bed layer through a pipeline, and the top outlet of the plate group fixing chamber is connected to a top coolant outlet of the plate fixed-bed carbonylation reactor through a pipeline.

As a preferred embodiment, the esterification reaction tower 9 is a packing tower.

As a preferred embodiment, the esterification reaction tower 9 is a tower plate-packing combined tower having a tower plate portion and a packing packed portion.

As a preferred embodiment, the methanol washing tower 7, the methanol rectification tower 5, the methanol recovery tower 11, the NO recovery tower 13, the MN recovery tower 15, the DMO rectification tower 6 and the nitric acid concentration tower 12 are packing towers, plate towers or bubble towers.

As a preferred embodiment, packing packed in the packing towers is random packing or high efficiency structured packing; a shape of the random packing is a saddle shape, Raschig ring, Pall ring, wheel ring, intalox saddle ring, spherical shape or columnar shape; and the high efficiency structured packing is corrugated packing, grid packing or impulse packing.

The hydrogenation reactor 17 is a plate reactor, a tube reactor or a tube-plate combined reactor.

As a preferred embodiment, the hydrogenation reactor 17 is a plate fixed-bed hydrogenation reactor;

a center of the plate fixed-bed hydrogenation reactor is provided with a plate group fixing chamber, a plate group is provided in the plate group fixing chamber and the plate group fixing chamber is further provided with a bottom inlet and a top outlet; a catalyst bed layer is provided between an outer wall of the plate group fixing chamber and an inner wall of the plate fixed-bed hydrogenation reactor; the catalyst bed layer is packed with a hydrogenation reaction catalyst and the catalyst bed layer is further provided with a top inlet and a bottom outlet; at a bottom of the plate fixed-bed hydrogenation reactor, a bottom coolant inlet of the plate fixed-bed hydrogenation reactor is connected to the bottom inlet of the plate group fixing chamber through a pipeline, and the bottom outlet of the catalyst bed layer is connected to the bottom discharge outlet of the plate fixed-bed hydrogenation reactor through a pipeline; and at a top of the plate fixed-bed hydrogenation reactor, a top feed inlet of the plate fixed-bed hydrogenation reactor is connected to the top inlet of the catalyst bed layer through a pipeline, and the top outlet of the plate group fixing chamber is connected to a top coolant outlet of the plate fixed-bed hydrogenation reactor through a pipeline.

As a preferred embodiment, the membrane separator 28 consists of 1-100 hollow fiber membrane modules connected in parallel or in series.

As illustrated in FIG. 1 and FIG. 2, the flow of the method for producing dimethyl oxalate through high-pressure carbonylation of industrial synthesis gas and producing ethylene glycol through dimethyl oxalate hydrogenation provided by the present invention is as follow:

NO coming from a pipe 18, fresh methanol coming from a pipe 26 and $O_2$ fed through 2-8 loops are in gas-liquid countercurrent contact in an esterification reaction tower 9 to perform an esterification reaction, MN mixed gas produced at a tower top and recovered gas of a pressure swing adsorption tank coming from a pipe 39 get together and then enter a dehydration tower 10 through a pipe 24 to perform dehydration treatment, dried gas obtained after dehydration is mixed with CO coming from a pipe 1 and $N_2$ coming from a pipe 2 through a pipe 25, and then mixed gas is used as carbonylation reaction raw material gas and enters a pipe 3. Located at a tower bottom of the esterification reaction tower 9 is acidic waste liquid containing a great amount of methanol, and except a certain amount of acidic waste liquid which refluxes to the esterification reaction tower 9 through a pipe 20, other acidic waste liquid together with methanol-containing acidic waste liquid coming from a pipe 33 enters a methanol recovery tower 11 through a pipe 21 to perform methanol recovery; methanol light components produced at a tower top of the methanol recovery tower 11 pass through a pipe 28 and then are divided, and except a part which enters an MN recovery tower 15 as washing liquid through a pipe 29, the other part and the fresh methanol coming from the pipe 26 get together and then are used as an alcohol resource of the esterification reaction tower 9 through a pipe 22; and acid-containing waste water produced at a tower bottom of the methanol recovery tower 11 enters a nitric acid concentration tower 12 through a pipe 27 to perform nitric acid concentration.

The carbonylation reaction raw materials coming from the pipe 3 exchange heat with carbonylation reaction products discharged from a bottom of a carbonylation reactor 1 through an outlet heat exchanger I 3, and then enter a catalyst bed layer from a top of the carbonylation reactor 1 to perform a carbonylation reaction; and simultaneously, refined water coming from the outside of the system enters a steam drum I 2 through a pipe 8, coolants in the steam drum I 2 enter a plate group fixing chamber from a bottom of the carbonylation reactor 1 and exchange heat with the catalyst bed layer to remove heat produced during the reaction, the heated coolants are steam-liquid mixture, are introduced outside from the top of the carbonylation reactor 1 and then enter the steam drum I 2 to perform gas-liquid separation, and produced low-pressure saturated steam enters an external low-pressure steam recovery system through a pipe 7 to realize recycling. The carbonylation reaction products exchange heat through the outlet heat exchanger I 3 and then enter a first gas-liquid separator 4 to perform gas-liquid separation, and gas phase components containing most DMC (dimethyl carbonate) enter a methanol washing tower 7 through a pipe 11 and are in countercurrent contact with recovered methanol coming from a pipe 57; DMO heavy components at a bottom of the first gas-liquid separator 4 and methanol washing liquid containing MN (methyl nitrite), DMC and DMO (dimethyl oxalate) at a tower bottom of the methanol washing tower 7 enter a methanol rectification tower 5 respectively through a pipe 10 and a pipe 12, and two material flows are in countercurrent contact to perform extraction and separation; most of gas phase light components at a tower top of the methanol washing tower 7 pass through a carbonylation recycle compressor 8 and enter the esterification reaction tower 9 for recycling through a pipe 17, and a small part is used as purge gas which enters an NO recovery tower 13 through a pipe 32 to perform recovery treatment; methanol and methyl nitrite mixture recovered at a tower top of the methanol rectification tower 5 is cycled to the esterification reaction tower for reuse through a pipe 14, and heavy components at a tower bottom enter a DMO rectification tower 6 through a pipe 13; DMC products are obtained at a tower top of the DMO rectification tower 6, and dimethyl oxalate components at a tower bottom enter a pipe 15 and are used as raw materials for a hydrogenation reaction.

Located at a tower top of the nitric acid concentration tower 12 is mainly acid-containing waste water, which is drained to an external area through a pipe 30 to perform environmental-friendly treatment, and concentrated nitric acid at a tower bottom enters the NO recovery tower 13 through a pipe 31, is used as an acid source and is in countercurrent contact with recovered methanol coming from the pipe 57 and the purge gas coming from the pipe 32 to perform an esterification regeneration reaction to recover NO in the purge gas; methanol-containing nitric acid waste liquid at a tower bottom of the NO recovery tower 13 enters the methanol recovery tower 11 through the pipe 33 to realize recycling, and MN-containing light components produced at a tower top are pressurized through a compressor 14 and then enter the MN recovery tower 15. In the MN recovery tower 15, the MN-containing light components are in countercurrent contact with the recovered methanol coming from the pipe 29, MN therein is eluted and enters the esterification reaction tower 9 from a tower bottom through a pipe 36, gas phase light components at a tower top enter a pressure swing adsorption tank 16 through a pipe 37 to perform pressure swing adsorption, CO-containing mixed gas after $CO_2$ is removed enters the dehydration tower 10 through the pipe 39, and the removed $CO_2$ gas may be exhausted to an external area to perform treatment.

Industrial hydrogen coming from a pipe 54 and recycled gas coming from a pipe 53 are mixed, then are pressurized through a hydrogenation recycle compressor 25 and then enter a pipe 55, then mixed gas is mixed with the dimethyl oxalate components coming from the pipe 15 and recovered hydrogen coming from a pipe 68 to obtain mixture which is used as hydrogenation reaction raw materials, and the mixture enters an outlet heat exchanger II 20 through a pipe 40, exchanges heat with hydrogenation reaction products introduced outside from a bottom of a hydrogenation reactor 17 and then enters a catalyst bed layer from a top of the hydrogenation reactor 17 to perform a catalytic hydrogenation reaction; and simultaneously, refined water coming from the outside of the system enters a steam drum II 18 through a pipe 48, coolants in the steam drum II 18 enter a plate group fixing chamber from a bottom of the hydrogenation reactor 17 through a pipe 49 and exchange heat with the catalyst bed layer to remove heat produced during the reaction, the heated coolants are steam-liquid mixture, are introduced outside from the top of the hydrogenation reactor 17 and then enter the steam drum II 18 to perform gas-liquid separation, and produced low-pressure saturated steam enters an external low-pressure steam recovery system through a pipe 47 to realize recycling. Hydrogenation reaction products enter a high-pressure gas-liquid separator 21 through a pipe 44 after heat exchanging to perform gas-liquid separation, a gas phase passes through a pipe 51, then most of the gas phase is used as recycled gas to enter the pipe 53 for recycling, and the remaining part of gas enters a low-pressure gas-liquid separator 26 through a pipe 52 to perform gas-liquid separation; liquid phase methanol in the low-pressure gas-liquid separator 26 flows out through a pipe 64, a gas phase and non-condensable gas coming from a pipe 58 get together through a pipe 65 and then enter a methanol absorption tank 27 through a pipe 66 to further remove methanol, gas obtained after liquid is removed enters a membrane separator 28 through a pipe 67, and after recovery treatment performed by a membrane system, except a small part of non-condensable gas such as $CO_2$, CO and $CH_4$ which are exhausted from a pipe 69, most recovered $H_2$ is pressurized and then enters the pipe 68 for recycling.

Liquid phase ethylene glycol crude products separated by the high-pressure gas-liquid separator 21 flow out from a pipe 50, get together with the liquid phase methanol coming from the pipe 64 and then enter a methanol separation tower 22; a certain amount of non-condensable gas is exhausted from a tower top of the methanol separation tower 22 through the pipe 58 to perform recovery, liquid phase light components at the tower top enter the pipe 57, and a liquid phase at a tower bottom enters a light component rectification tower 23 through a pipe 56 to perform separation; light components such as light component ethanol and methyl glycolate at a tower top of the light component rectification tower 23 enter an external alcohol recovery device through a pipe 60 to perform recovery, polyol mixture at a tower bottom enters an ethylene glycol product tower 24 through a pipe 59 to perform further purification, mixed light components mainly containing 1,2-BDO and ethylene glycol are subjected to further recovery treatment through a pipe 63, ethylene glycol produced by an upper side line of a tower body is collected as products through a pipe 62, and mixture containing a small amount of ethylene glycol and ethylene glycol polycondensate at a tower bottom enters an external area to perform treatment.

At an initial stage of startup, a startup heater 19 is used for heating the hydrogenation reaction raw materials, low-pressure steam is used as a heat source, the hydrogenation raw materials coming from the pipe 40 enter a pipe 45, are preheated by the startup heater 19 to inlet temperature of the bed layer and then enter the catalyst bed layer from the top of the hydrogenation reactor 17 through a pipe 46 and a pipe 42 to perform a hydrogenation reaction.

An example for performing industrial production by adopting the above-mentioned method flow is as follow:

Light components (components: 5.22 v % of MN, 22.12 v % of CO, 58.5 v % of $N_2$, 11.14 v % of NO, 0.63 v % of $CO_2$, 1.57 v % of methanol and 0.82 v % of others) coming from the tower top of the methanol washing tower and NO coming from the external area are mixed, then the mixture enters the esterification reaction tower 9 (inner diameter: 50 mm, height: 2600 mm, theoretical tower plate number:25, tower plate structure: packing tower) and are fed from a 25th tower plate, and $O_2$ enters the esterification reaction tower 9 in three loops respectively from 22th, 23th and 25th tower plates and is in gas-liquid countercurrent contact with fresh methanol fed from a 1st tower plate at the tower top, recovered methanol mixed liquid coming from the methanol recovery tower 11, methanol and methyl nitrite mixture fed from 5th tower plate and recovered from the methanol rectification tower 5, alcohol solution containing methyl nitrite coming from the tower bottom of the MN recovery tower 15 and tower bottom reflux liquid fed from 10th tower plate to perform an esterification reaction (wherein a molar ratio of $O_2$ to NO to methanol is 0.1:0.6:50). Tower top temperature of the esterification reaction tower 9 is 50° C., tower bottom temperature is 90° C., reaction area temperature is 70±10° C. and reaction pressure is 2 MPa. Discharged materials from the tower bottom of the esterification reaction tower 9 (components: 71.8 wt % of methanol, 8.0 wt % of MN and 20.2 wt % of other heavy components such as acid and water produced during reaction) are collected and then enter the methanol recovery tower 11 for is recovery treatment. Gas phase components (components: 10.05 v % of MN, 26.42 v % of CO, 55.88 v % of $N_2$, 5.2 v % of NO, 0.60 v % of $CO_2$, 1.57 v % of methanol and 0.28 v % of others) at the tower top of the esterification reaction tower 9 enter the dehydration tower 10 for dehydration. After dehydration performed by the dehydration tower 10 (absorbent: 4 A molecular sieve, operating temperature: 43° C., pressure: 1.9 MPa, wherein a molecular sieve dryer A and a molecular sieve dryer B are alternatively run and regenerated), dried gas with water content of 60 ppm is obtained.

Acid-containing waste alcohol liquid at the tower bottom of the esterification reaction tower 9 enters the methanol recovery tower 11 (inner diameter: 50 mm, height: 2100 mm, theoretical tower plate number:20, packed with high efficiency structured packing, tower top temperature: 120° C., tower bottom temperature: 140° C., tower top pressure: 0.7 MPa and reflux ratio of tower top light components: 1.2), located at the tower top are methanol-containing light components (components: 90 wt % of methanol, 8 wt % of MN, 2 wt % of $H_2O$), a part of which (accounting for 75 wt %) gets together with replenished fresh methanol and enters the top of the esterification reaction tower 9, and the remaining part is used as washing liquid in the MN recovery tower 15; and acid-containing waste water at the tower bottom of the methanol recovery tower 11 enters the nitric acid concentration tower 12 to perform nitric acid concentration.

The center of the carbonylation reactor 1 (plate fixed-bed reactor, inner diameter: 320 mm, height: 2000 mm) is provided with a plate group fixing chamber, three groups of plates are provided in the plate group fixing chamber, and each group has three plates; and a catalyst bed layer is provided between the outer wall of the plate group fixing chamber and the inner wall of the carbonylation reactor 1 and is packed with a high-pressure reaction catalyst (commercially available catalyst produced by Shanghai Wuzheng Engineering Technology Co., Ltd., an product model of which is DMO-0701T). Dried gas coming from the dehydration tower 10 is mixed with dehydrogenated industrial CO (99 v %) used as carbonylation reaction raw materials and nitrogen used as an inert gas source, and then the mixture exchanges heat with carbonylation reaction products through the outlet heat exchanger I 3, then is preheated to 95° C., firstly enters from the top of the carbonylation reactor 1 and then enters the catalyst bed layer in a radial flow way to perform a carbonylation reaction (catalyst bed layer hotspot temperature: 130° C., reaction pressure: 1.8 MPa, gas hourly space velocity: 10000 $h^{-1}$); and the carbonylation products then enter the outlet heat exchanger 3 to exchange heat and then enter the first gas-liquid separator 4, at which gas-liquid separation is performed.

Coolant in the plate group fixing chamber of the carbonylation reactor 1 is water medium, refined water coming from the outside of the system enters the steam drum I 2 to replenish water, the water in the steam drum I enters the plate group fixing chamber in the carbonylation reactor 1 to exchange heat with the catalyst bed layer to remove heat produced during the reaction, heated water is steam-liquid mixture and enters the steam drum to perform gas-liquid separation, and produced low-temperature saturated steam is delivered to an external low-pressure steam pipe network to realize recycling.

A liquid phase (methanol: 1.16 wt %, DMC: 0.45 wt %, DMO: 97.6 wt %, others: 0.79 wt %) introduced outside from the first gas-liquid separator 4 is used as an extraction agent and enters the methanol rectification tower 5 to perform separation; DMC-containing mixed gas phase components which are introduced outside enter the methanol washing tower 7 (inner diameter: 50 mm, height: 3200 mm, theoretical plate number: 30, packed with high efficiency structured packing, tower top temperature: 28.1° C., tower bottom temperature: 39.8° C., tower top pressure: 1.5 MPa) and are in countercurrent contact with the recovered methanol (content: 99.9 wt %) coming from the methanol separation tower 22 to elute DMC and DMO in the mixed gas, most of the gas phase light components at the top of the methanol washing tower 7 enter the esterification reaction tower 9 through the carbonylation recycle compressor 8 to recycle nitric oxides produced during the carbonylation reaction; a small part of non-condensable gas (accounting for 0.5 v %) is used as purge gas and enters the NO recovery tower 13 to perform recovery treatment; and a liquid phase at the tower bottom of the methanol washing tower 7 enters the methanol rectification tower 5 to perform separation.

Light components (methanol: 88.2 wt %, MN: 11.8 wt %) at the tower top of the methanol rectification tower 5 (inner diameter: 50 mm, height: 2600 mm, extraction rectification tower, theoretical plate number: 25, packed with high efficiency structured packing, tower top temperature: 73.12° C., tower bottom temperature: 185.0° C., tower top pressure: 0.1 MPa) enter the esterification reaction tower 9 and are used as one of alcohol sources, and heavy components containing DMC and DMO at the tower bottom enter the DMO rectification tower 6 to perform separation.

DMC at the tower top of the DMO rectification tower 6 (inner diameter: 50 mm, height: 3000 mm, theoretical plate number 28, packed with high efficiency structured packing, tower top temperature: 103° C., tower bottom temperature: 180° C., operated at normal temperature, reflux ratio: 50) is collected as products (DMC product purity: 99.41 wt %); and heavy components (DMO purity: 99.9 wt %) at the tower bottom are all used as raw materials at the hydrogenation section.

In the nitric acid concentration tower 12 (inner diameter: 32 mm, height: 850 mm, theoretical tower plate number: 8, packaged with high efficiency structured packing, tower top temperature: 64° C., tower bottom temperature: 87° C., tower top pressure: 0.15 MPa, reflux ratio: 0.05), located at the tower top is mainly acid-containing waste water which is drained to an external area to perform environmental-friendly treatment, and concentrating performed at the tower bottom produces concentrated nitric acid with concentration of 68 wt %, which is used as an acid source of the NO recovery tower 13.

In the NO recovery tower 13 (inner diameter: 32 mm, height: 2100 mm, theoretical plate number:20, packed with high efficiency structured packing, tower top temperature: 50° C., tower bottom temperature: 100° C., tower top pressure: 1.4 MPa), the purge gas coming from the methanol washing tower 7 is fed from a 20th tower plate, and the recovered methanol (99.9 wt %) fed from a 1st tower plate and coming from the methanol separation tower 22 and the concentrated nitric acid fed from an 6th tower plate and coming from the nitric acid concentration tower 12 are in countercurrent contact to perform esterification regeneration reaction. A molar ratio of NO in the purge gas to $HNO_3$ in the concentrated nitric acid to methanol is 1:2.5:20. Light components (components: 21.1 v % of CO, 0.6 v % of $CO_2$, 20.8 v % of MN, 55.7 v % of $N_2$, 1.8 v % of methanol) at the tower top of the NO recovery tower 13 are pressurized by the compressor 14 and then enter the MN recovery tower 15; and heavy components (components: 71.8 wt % of methanol and 28.2 wt % other heavy components such as acid and water produced during reaction) at the tower bottom of the NO recovery tower enter a 3rd tower plate of the methanol recovery tower 11 to realize recovery.

A feed material in the MN recovery tower 15 (inner diameter: 32 mm, height: 3200 mm, theoretical plate number: 30, packed with high efficiency structured packing, tower top temperature: 30.8° C., tower bottom temperature: 41.3° C., tower top pressure: 2 MPa) is in countercurrent contact with the recovered methanol fed from a 1st tower plate and coming from the methanol recovery tower 11 to absorb a great amount of MN in inlet gas, other gases (components: 27.3 v % of CO, 0.8 v % of $CO_2$, 71.9 v % of $N_2$) enter the pressure swing adsorption tank 16 from the tower top, and the materials (components: 79.3 mol % of methanol, 20.7 mol % of MN) in the tower bottom enter a 5th tower plate of the esterification reaction tower 9 to realize recycling. The gas phase at the tower top of the MN recovery tower 15 is subjected to pressure swing adsorption performed by the pressure swing adsorption tank 16, purified gas ($N_2$: 72 v %, CO: 28 v %) enters the dehydration tower 10 for treatment and then enters the carbonylation reactor 1, and 0.95 v % of gas (components: 99.8 v % of $CO_2$) is exhausted to an external area to perform treatment.

The center of the hydrogenation reactor 17 (plate fixed-bed hydrogenation reactor, inner diameter: 325 mm, height: 900 mm) is provided with a plate group fixing chamber, three groups of plates are provided in the plate group fixing chamber, and each group has three plates; and a catalyst bed layer is provided between the outer wall of the plate group fixing chamber and the inner wall of the hydrogenation reactor and is packed with a hydrogenation reaction catalyst (commercially available catalyst produced by Shanghai Wuzheng Engineering Technology Co., Ltd., an product model of which is MEG-801T).

Industrial $H_2$ (purity: 99.9 v %) and the recycled gas (components: 96 v % of hydrogen, 0.05 v % of methanol, 0.02 v % of nitrogen, 0.02 v % of carbon monoxide, 3 v % of methanol, 0.91 v % of others) coming from the high-pressure gas-liquid separator 21 are compressed by the hydrogenation recycle compressor 25 and then get together with the dimethyl oxalate (99.9 wt %) coming from the tower bottom of the DMO rectification tower 6, and then the mixture enters the outlet heat exchanger II 20 of the hydrogenation plate reactor 17, is preheated to 175° C., firstly the mixture enters from the top of the hydrogenation reactor 17 and then enters the catalyst bed layer in a radial flow way to perform a hydrogenation reaction (catalyst bed layer hotspot temperature: 190° C., reaction pressure: 3.0 MPa, liquid hourly space velocity: 2.8 Kg/Kg·h); and the hydrogenation products are discharged from the bottom, then enter the outlet heat exchanger II 20 to exchange heat and then enter the high-pressure gas-liquid separator 21, at which gas-liquid separation is performed.

At an initial stage of startup, the materials passing through the outlet heat exchanger II 20 enter the startup heater 19 to perform preheating, the preheated gas is used as raw material gas, and after the inlet temperature of the catalyst bed layer is reached, the raw material gas enters the catalyst bed layer to perform a hydrogenation reaction.

Coolant in the plate group fixing chamber of the hydrogenation reactor 17 is water medium, refined water coming from the outside of the system enters the steam drum II 18 to replenish water, the water in the steam drum II 18 enters the plate group fixing chamber in the hydrogenation reactor 17 to exchange heat with the catalyst bed layer to remove heat produced during the reaction, heated water is steam-liquid mixture and enters the steam drum II to perform gas-liquid separation, and produced low-temperature saturated steam is delivered to an external low-pressure steam pipe network to realize recycling.

After the hydrogenation products are separated by the high-pressure gas-liquid separator 21, the most gas phase is used as recycled gas and enters the hydrogenation recycle compressor 25, the remaining non-condensable gas (accounting for 1.2 v %) enters the low-pressure gas-liquid separator 26, and a liquid phase (methanol: 50.1 wt %, ethylene glycol: 48.55 wt %, methyl glycolate: 0.06 wt %, ethanol: 0.39 wt %, BDO: 0.12 wt %, others: 0.78 wt %) introduced outside from the high-pressure gas-liquid separator 21 enters the methanol separator tower 22 to perform separation. A liquid gas separated by the low-pressure gas-liquid separator 26 enters the methanol separation tower 22 to perform separation, a gas phase is treated through the methanol absorption tank 27 (inner diameter: 160 mm, height: 900 mm) to further remove methanol, and then a gas phase therein (components: 97 v % of hydrogen, 0.15 v % of methanol, 0.06 v % of nitrogen, 0.27 v % of carbon monoxide and 2.52 v % of others) enters the membrane separator 28 to realize recycling. Hydrogen (purity: 99.9 v %) separated by the membrane separator is preheated through the outlet heat exchanger II and then enters the hydrogenation plate reactor 17, and only a small part of non-condensable gas rich in methane and the like is used as purge gas and is exhausted to an external area to realize recycling.

In the methanol separation tower 22 (inner diameter: 50 mm, height: 2600 mm, theoretical plate number:25, packed with high efficiency structured packing, tower top temperature: 50.82° C., tower bottom temperature: 171° C., tower top absolute pressure: 90 kPa), materials are fed from a 12th tower plate, non-condensable gas at the tower top enters the methanol absorption tank 27 for treatment and then enters the membrane separator 28, a tower top reflux ratio is 1.6, and discharged materials (99.9 wt % of methanol and 0.1 wt % of other low-boiling-point components) from the tower top are collected and then respectively enter the methanol washing tower 7 and the NO recovery tower 13; and heavy components (components: 96 wt % of ethylene glycol, 0.12 wt % of methyl glycolate, 2.68 wt % of 1, 2-BDO, 0.8 wt % of ethanol, 0.4 wt % of other components) at the tower bottom of the methanol separation tower 22 enter the light component rectification tower 23.

Ethanol crude products (98 wt % of ethanol and 2 wt % of methyl glycolate) are introduced outside from the tower top of the light component rectification tower 23 (inner diameter: 50 mm, height: 4000 mm, theoretical plate number:40, packed with high efficiency structured packing, tower top temperature: 83.8° C., tower bottom temperature: 146.9° C., tower top absolute pressure: 16 kPa, tower top reflux ratio: 50) and are delivered to an external area to perform collection treatment; and heavy components (97.9 wt % of ethylene glycol, 2.1 wt % of 1, 2-BDO) at the tower bottom are delivered to the ethylene glycol product tower 24.

In the ethylene glycol product tower 24 (inner diameter: 50 mm, height: 6500 mm, theoretical tower plate number: 60, packed with high efficiency structured packing, tower top temperature: 130° C., tower bottom temperature: 170.1° C., tower top absolute pressure: 5 kPa, a tower top reflux ratio is 98, components (components: 19.79 wt % of 1, 2-BDO, 80 wt % of ethylene glycol, 0.21 wt % of others) at the tower top are collected to an external area and are recovered as byproducts, a small amount of ethylene glycol and ethylene glycol polycondensate at the tower bottom are delivered to an external area for treatment, and final products ethylene glycol (content: 99.99 wt %) are collected from a 5th tower plate of the side line of the tower body of the ethylene glycol product tower 24.

The above-mentioned embodiments are just used for exemplarily describing the principle and effects of the present invention instead of limiting the present invention. One skilled in the art may make modification or variation the above-mentioned embodiments without departing from the spirit and scope of the present invention. Therefore, all equivalent modifications or variations made by those who have common knowledge in the art without departing from the spirit and technical concept disclosed by the present invention shall still be covered by the claims of the present invention.

What is claimed is:

1. A method for producing dimethyl oxalate through carbonylation of industrial synthesis gas and producing ethylene glycol through dimethyl oxalate hydrogenation, comprising the following steps that:
   (1) industrial NO (nitric oxide), $O_2$ and methanol are fed into an esterification reaction tower to perform an esterification reaction; methyl nitrite mixed gas at a tower top of the esterification reaction tower is fed into a carbonylation reactor to perform a carbonylation reaction; a part of acidic alcohol solution at a tower bottom of the esterification reaction tower refluxes to the esterification reaction tower, and a part of the acidic alcohol solution is fed into a methanol recovery tower; a part of methanol recovered at a tower top of the methanol recovery tower is cycled to the esterification reaction tower for recycling, and the other part of the methanol enters an MN (methyl nitrite) recovery tower as washing solution; and waste acid at a tower bottom of the methanol recovery tower enters a nitric acid concentration tower to perform concentration treatment;
   (2) the methyl nitrite coming from the esterification reaction tower and industrial CO and $N_2$ feed enter the carbonylation reactor to perform a carbonylation reaction under the existence of a carbonylation reaction catalyst, wherein carbonylation reaction temperature is 30-200° C., reaction pressure is 1-10 MPa and gas hourly space velocity is 3000-30000 $h^{-1}$;
   (3) carbonylation products enter a first gas-liquid separator to perform gas-liquid separation, a gas phase enters a methanol washing tower and a liquid phase enters a methanol rectification tower; a part of gas phase components at a tower top of the methanol washing tower is cycled to the esterification reaction tower, and a part of the gas phase components enters an NO (nitric oxide) recovery tower as purge gas to perform recovery treatment; liquid phase components at a tower bottom of the methanol washing tower enter the methanol rectification tower to perform rectification and separation; methanol and methyl nitrite mixture recovered at a tower top of the methanol rectification tower is cycled to the esterification reaction tower for recycling, and heavy components at a tower bottom enter a DMO (dimethyl oxalate) rectification tower; and DMC (dimethyl carbonate) products are obtained at a tower top of the DMO (dimethyl oxalate) rectification tower, and dimethyl oxalate components at a tower bottom enter a hydrogenation reactor to perform a hydrogenation reaction;
   (4) the waste acid coming from the methanol recovery tower is concentrated to nitric acid concentration of 10-68 wt % through the nitric acid concentration tower, and then the waste acid is cycled to the NO (nitric oxide) recovery tower; concentrated nitric acid, methanol and purge gas coming from the methanol washing tower experience an esterification regeneration reaction in the NO (nitric oxide) recovery tower; gas phase light components at a tower top of the NO (nitric oxide) recovery tower enter the MN (methyl nitrite) recovery tower, and methanol-containing nitric acid waste liquid produced at a tower bottom is cycled to the methanol recovery tower to perform further recovery treatment; gas phase feed obtained after recovered methanol washing in the MN (methyl nitrite) recovery tower enters a pressure swing adsorption tank, and methyl nitrite-containing alcohol solution at a tower bottom of the MN (methyl nitrite) recovery tower enters the esterification reaction tower; and $CO_2$ separated by the pressure swing adsorption tank is exhausted to an external device for treatment, and recovered $N_2$ and CO purified gas enter the carbonylation reactor for recycling;

(5) the dimethyl oxalate components coming from the DMO (dimethyl oxalate) rectification tower are mixed with industrial hydrogen pressurized by a hydrogenation recycle compressor, then the mixtures enters the hydrogenation reactor, and a hydrogenation reaction is performed under the existence of a hydrogenation catalyst to produce methanol, ethylene glycol, etc., wherein hydrogenation reaction temperature is 160-320° C., reaction pressure is 1-10 MPa and liquid hourly space velocity is 1-3 Kg/Kg·h; and (6) hydrogenation products enter a second gas-liquid separator to perform gas-liquid separation, a part of a gas phase is pressurized through the hydrogenation recycle compressor and then is cycled to the hydrogenation rector, the other part of the gas phase enters a membrane separator to perform recovery treatment, then returns to the hydrogenation reactor for recycling, and a liquid phase enters an ethylene glycol product tower to perform separation to obtain ethylene glycol products.

2. The method for producing dimethyl oxalate through carbonylation of industrial synthesis gas and producing ethylene glycol through dimethyl oxalate hydrogenation according to claim 1, characterized in that the method further comprises one or more steps selected from the group consisting of:

(I) the carbonylation reactor is externally connected to a dehydration tower; and the gas phase recovered by the pressure swing adsorption tank and the methyl nitrite mixed gas coming from the tower top of the esterification reaction tower are dehydrated by the dehydration tower and then enter the carbonylation reactor to perform the carbonylation reaction;

(II) the carbonylation reactor is externally connected to an outlet heat exchanger I; and the industrial CO and $N_2$ and dried gas coming from the dehydration tower are used as carbonylation reaction raw materials, exchange heat with the carbonylation reaction products coming from the carbonylation reactor through the outlet heat exchanger I and then enter the carbonylation reactor to perform the carbonylation reaction;

(III) the part of gas phase components coming from the tower top of the methanol washing tower is pressurized by a carbonylation recycle compressor and then enters the esterification reaction tower;

(IV) the hydrogenation reactor is externally connected to an outlet heat exchanger II; and the dimethyl oxalate components coming from the DMO (dimethyl oxalate) rectification tower, the industrial hydrogen and recycled gas coming from a pressurization recycle compressor and recovered gas coming from the membrane separator are used as hydrogenation reaction raw materials, exchange heat with the hydrogenation products coming from the hydrogenation reactor through the outlet heat exchanger II and then enter the hydrogenation reactor to perform the hydrogenation reaction;

(V) the gas phase light components at the tower top of the NO (nitric oxide) recovery tower are compressed and pressurized by a compressor and then enter the MN (methyl nitrite) recovery tower; and (VI) a liquid phase separated by the second gas-liquid separator firstly enters a methanol separation tower; non-condensable gas recovered at a tower top of the methanol separation tower enters the membrane separator, a part of liquid phase light components such as methanol recovered at the top of the methanol separation tower enters an upper portion of the methanol washing tower as washing liquid, and the other part enters the NO (nitric oxide) recovery tower; liquid phase heavy components at a tower bottom of the methanol separation tower enter a light component rectification tower to perform further separation and purification; light components at a tower top of the light component rectification tower enter an external alcohol recovery device to perform recovery treatment; heavy components at a tower bottom of the light component rectification tower enter the ethylene glycol product tower; and light components at a tower top of the ethylene glycol product tower enter an external 1,2-BDO recovery treatment device to perform further recovery treatment, heavy components at a tower bottom of the ethylene glycol product tower enter an external recovery treatment device to perform subsequent treatment, and ethylene glycol products are introduced out from an upper side line of the ethylene glycol product tower.

3. The method for producing dimethyl oxalate through carbonylation of industrial synthesis gas and producing ethylene glycol through dimethyl oxalate hydrogenation according to claim 2, characterized in that the dehydration tower consists of a molecular sieve dryer A and a molecular sieve dryer B which alternatively run and are regenerated; the molecular sieve dryer A and the molecular sieve dryer B are packed with adsorbents; the adsorbents are selected from a group consisting of 3 A molecular sieve, 4 A molecular sieve, 5 A molecular sieve, 9 A molecular sieve and calcium oxide; operating temperature of the molecular sieve dryer A and the molecular sieve dryer B is 40-260° C., and pressure is 1-10 MPa; and dried gas is obtained through treatment of the dehydration tower, and a content of water in the dried gas 0.1-100 ppm.

4. The method for producing dimethyl oxalate through carbonylation of industrial synthesis gas and producing ethylene glycol through dimethyl oxalate hydrogenation according to claim 2, characterized in that the second gas-liquid separator comprises a high-pressure gas-liquid separator and a low-pressure gas-liquid separator; a part of a gas phase separated by the high-pressure gas-liquid separator enters the hydrogenation recycle compressor and the other part enters the low-pressure gas-liquid separator; a liquid phase separated by the high-pressure gas-liquid separator enters the methanol separation tower; and a gas phase separated by the low-pressure gas-liquid separator enters the membrane separator, and a liquid phase separated by the low-pressure gas-liquid separator enters the methanol separation tower.

5. The method for producing dimethyl oxalate through carbonylation of industrial synthesis gas and producing ethylene glycol through dimethyl oxalate hydrogenation according to claim 4, characterized in that 0.1-10 v % of the gas phase separated by the high-pressure gas-liquid separator enters the low-pressure gas-liquid separator.

6. The method for producing dimethyl oxalate through carbonylation of industrial synthesis gas and producing ethylene glycol through dimethyl oxalate hydrogenation according to claim 4, characterized in that the gas phase separated by the low-pressure gas-liquid separator and the non-condensable gas coming from the methanol separation tower enter the membrane separator after methanol is absorbed by a methanol absorption tank.

7. The method for producing dimethyl oxalate through carbonylation of industrial synthesis gas and producing ethylene glycol through dimethyl oxalate hydrogenation according to claim 1, characterized in that the carbonylation reactor is a plate reactor, a tube reactor or a tube-plate combined reactor; and the hydrogenation reactor is a plate reactor, a tube reactor or a tube-plate combined reactor.

8. The method for producing dimethyl oxalate through carbonylation of industrial synthesis gas and producing ethylene glycol through dimethyl oxalate hydrogenation according to claim 7, characterized in that the method further comprises one or two steps selected from the group consisting of:
(I) the carbonylation reactor is a plate fixed-bed carbonylation reactor; a center of the plate fixed-bed carbonylation reactor is provided with a plate group fixing chamber, and a plate group is provided in the plate group fixing chamber; a catalyst bed layer is provided between an outer wall of the plate group fixing chamber and an inner wall of the plate fixed-bed carbonylation reactor; the catalyst bed layer is packed with a carbonylation reaction catalyst; after temperature of carbonylation reaction raw materials reaches inlet temperature of the catalyst bed layer, the carbonylation reaction raw materials enter the catalyst bed layer from a top of the plate fixed-bed carbonylation reactor to perform a carbonylation reaction; coolants introduced inside from the outside enter the plate group fixing chamber from a bottom of the plate fixed-bed carbonylation reactor and are introduced outside from the top of the plate fixed-bed carbonylation reactor, and heat exchange is performed in a backflow method to take away reaction heat produced during the carbonylation reaction; and carbonylation products coming from a bottom of the catalyst bed layer are introduced outside from the bottom of the plate fixed-bed carbonylation reactor; and
(II) the hydrogenation reactor is a plate fixed-bed hydrogenation reactor; a center of the plate fixed-bed hydrogenation reactor is provided with a plate group fixing chamber, and a plate group is provided in the plate group fixing chamber; a catalyst bed layer is provided between an outer wall of the plate group fixing chamber and an inner wall of the plate fixed-bed hydrogenation reactor; the catalyst bed layer is packed with a hydrogenation reaction catalyst; after temperature of hydrogenation reaction raw materials reaches inlet temperature of the catalyst bed layer, the hydrogenation reaction raw materials enter the catalyst bed layer from a top of the plate fixed-bed hydrogenation reactor to perform a hydrogenation reaction; coolants introduced inside from the outside enter the plate group fixing chamber from a bottom of the plate fixed-bed hydrogenation reactor and are introduced outside from the top of the plate fixed-bed hydrogenation reactor, and heat exchange is performed in a backflow method to take away reaction heat produced during the hydrogenation reaction; and hydrogenation products coming from a bottom of the catalyst bed layer are introduced outside from the bottom of the plate fixed-bed hydrogenation reactor.

9. The method for producing dimethyl oxalate through carbonylation of industrial synthesis gas and producing ethylene glycol through dimethyl oxalate hydrogenation according to claim 8, characterized in that the plate fixed-bed carbonylation reactor is externally connected to a steam drum I; coolants introduced inside from the outside enter the steam drum I, and the coolants in the steam drum I enter the plate group fixing chamber of the plate fixed-bed carbonylation reactor and exchange heat with the catalyst bed layer to remove reaction heat; and the heated coolants are steam-liquid mixture and enter the steam drum I to perform gas-liquid separation, and produced low-pressure saturated steam enters an external low-pressure steam recovery system for recycling;
the plate fixed-bed hydrogenation reactor is externally connected to a steam drum II; coolants introduced inside from the outside enter the steam drum II, and the coolants in the steam drum II enter the plate group fixing chamber of the plate fixed-bed hydrogenation reactor and exchange heat with the catalyst bed layer to remove reaction heat; and the heated coolants are steam-liquid mixture and enter the steam drum II to perform gas-liquid separation, and produced low-pressure saturated steam enters the external low-pressure steam recovery system for recycling.

10. The method for producing dimethyl oxalate through carbonylation of industrial synthesis gas and producing ethylene glycol through dimethyl oxalate hydrogenation according to claim 8, characterized in that the plate fixed-bed hydrogenation reactor is externally connected to a startup heater; at an initial stage of startup, hydrogenation reaction raw materials go out from the outlet heat exchanger II and then enter the startup heater to perform preheating, and after the inlet temperature of the catalyst bed layer is reached through preheating, the hydrogenation reaction raw materials enter the catalyst bed layer to perform a hydrogenation reaction; at the initial stage of startup, the startup heater provides a unique heat source for the hydrogenation reaction in the plate fixed-bed hydrogenation reactor; and a heat source of the startup heater is low-pressure steam.

11. The method for producing dimethyl oxalate through carbonylation of industrial synthesis gas and producing ethylene glycol through dimethyl oxalate hydrogenation according to claim 1, characterized in that a theoretical plate number of the esterification reaction tower is 20-50; in the feed of the esterification reaction tower, the $O_2$ is respectively fed from 16th-50th tower plates in 2-8 loops; the NO (nitric oxide) and the gas phase light components coming from the tower top of the methanol washing tower are fed from 18th-50th tower plates; the fresh methanol, the recovered methanol coming from the tower top of the methanol recovery tower, the recovered methanol and methyl nitrite mixture coming from the tower top of the methanol rectification tower and the methyl nitrite-containing alcohol solution coming from the tower bottom of the MN (methyl nitrite) recovery tower are fed from 1st-5th tower plates; reflux materials from the tower bottom of the esterification reaction tower are fed from 10th-25th tower plates;
a molar ratio of $O_2$ to NO to methanol in the esterification reaction tower is (0.01-0.8):(0.1-3.2):(0.8-50); and tower top temperature of the esterification reaction tower is 30-80° C., tower bottom temperature is 50-200° C., reaction area temperature is 50-160° C. and reaction pressure is 0.5-10 MPa.

12. The method for producing dimethyl oxalate through carbonylation of industrial synthesis gas and producing ethylene glycol through dimethyl oxalate hydrogenation according to claim 1, characterized in that a theoretical tower plate number of the methanol recovery tower is 5-50, tower top temperature is 40-150° C., tower bottom temperature is 60-230° C. and tower top pressure is 0.1-2.0 MPa; a reflux ratio of the light components at the tower top of the methanol recovery tower is 0.1-3.0; and a proportion of the part, which cyclically enters the esterification reaction tower, in the recovered methanol at the tower top of the methanol recovery tower is 10-90 wt %.

13. The method for producing dimethyl oxalate through carbonylation of industrial synthesis gas and producing ethylene glycol through dimethyl oxalate hydrogenation according to claim 1, characterized in that a theoretical tower plate number of the methanol washing tower is 10-50, tower top temperature is 15-70° C., tower bottom temperature is 10-100° C. and tower top pressure is 0.9-10 MPa; and a proportion of the purge gas in the gas phase components at the tower top of the methanol washing tower is 0.05-5 v %.

14. The method for producing dimethyl oxalate through carbonylation of industrial synthesis gas and producing ethylene glycol through dimethyl oxalate hydrogenation according to claim 1, characterized in that the methanol rectification tower is an extraction rectification tower, a theoretical tower plate number is 10-60, tower top temperature is 50-150° C., tower bottom temperature is 130-250° C. and tower top pressure is 0.01-0.5 MPa.

15. The method for producing dimethyl oxalate through carbonylation of industrial synthesis gas and producing ethylene glycol through dimethyl oxalate hydrogenation according to claim 1, characterized in that a theoretical tower plate number of the nitric acid concentration tower is 1-30, tower top temperature is 30-110° C., tower bottom temperature is 60-160° C. and tower top pressure is 0.01-0.3 MPa; and a reflux ratio of the light components at the tower top of the nitric acid concentration tower is 0.01-3.

16. The method for producing dimethyl oxalate through carbonylation of industrial synthesis gas and producing ethylene glycol through dimethyl oxalate hydrogenation according to claim 1, characterized in that a theoretical tower plate number of the NO (nitric oxide) recovery tower is 5-30, tower top temperature is 30-120° C., tower bottom temperature is 50-200° C. and tower top pressure is 1-10 MPa; the purge gas is fed from 5th-30th tower plates of the NO (nitric oxide) recovery tower; the concentrated nitric acid is fed from 1st-10th tower plates of the NO (nitric oxide) recovery tower; the recovered methanol coming from the tower top of the methanol separation tower is fed from 1st-10th tower plates; and a molar ratio of nitric acid to methanol to NO in purge gas in the NO (nitric oxide) recovery tower (13) is (1.1-10):(2-100):(1-5).

17. The method for producing dimethyl oxalate through carbonylation of industrial synthesis gas and producing ethylene glycol through dimethyl oxalate hydrogenation according to claim 1, characterized in that a theoretical tower plate number of the MN (methyl nitrite) recovery tower is 10-60, tower top temperature is 0-50° C., tower bottom temperature is 0-80° C. and reaction pressure is 1-10 MPa.

18. The method for producing dimethyl oxalate through carbonylation of industrial synthesis gas and producing ethylene glycol through dimethyl oxalate hydrogenation according to claim 1, characterized in that a theoretical tower plate number of the DMO (dimethyl oxalate) rectification tower is 10-50, tower top temperature is 80-120° C., tower bottom temperature is 120-200° C. and operation is performed at normal pressure or reduced pressure; and a reflux ratio of the light components at the tower top of the DMO (dimethyl oxalate) rectification tower is 0.1-100.

19. The method for producing dimethyl oxalate through carbonylation of industrial synthesis gas and producing ethylene glycol through dimethyl oxalate hydrogenation according to claim 2, characterized in that a theoretical tower plate number of the methanol separation tower is 10-40, tower top temperature is 40-70° C., tower bottom temperature is 80-180° C. and operation is performed at normal pressure or reduced pressure; and a reflux ratio of the light components at the tower top of the methanol separation tower is 0.1-3.

20. The method for producing dimethyl oxalate through carbonylation of industrial synthesis gas and producing ethylene glycol through dimethyl oxalate hydrogenation according to claim 2, characterized in that a theoretical tower plate number of the light component rectification tower is 10-60, tower top temperature is 58-90° C., tower bottom temperature is 70-160° C. and tower top absolute pressure is 5-50 KPa; and a reflux ratio of the light components at the tower top of the light component rectification tower is 1-50.

21. The method for producing dimethyl oxalate through carbonylation of industrial synthesis gas and producing ethylene glycol through dimethyl oxalate hydrogenation according to claim 2, characterized in that a theoretical tower plate number of the ethylene glycol product tower is 30-100, tower top temperature is 100-150° C., tower bottom temperature is 130-230° C. and tower top absolute pressure is 5-50 KPa; and a reflux ratio of the light components at the tower top of the ethylene glycol product tower is 50-200 or total reflux.

22. The method for producing dimethyl oxalate through carbonylation of industrial synthesis gas and producing ethylene glycol through dimethyl oxalate hydrogenation according to claim 1, characterized in that components of purified gas recovered in the pressure swing adsorption tank comprise 60-80 v % of $N_2$ and 20-40 v % of CO; and separated $CO_2$ gas accounts for 0.1-5 v % of total amount of inlet gas, wherein a concentration of $CO_2$ is 99.8-99.9 v %.

23. The method for producing dimethyl oxalate through carbonylation of industrial synthesis gas and producing ethylene glycol through dimethyl oxalate hydrogenation according to claim 2, characterized in that the membrane separator consists of a plurality of hollow fiber membrane modules connected in parallel or in series; a concentration of hydrogen in purified gas obtained through separation and purification performed by the membrane separator is 88-99.99 v %, and a hydrogen recovery rate is 90-98.5%.

24. A device system for producing dimethyl oxalate through carbonylation of industrial synthesis gas and producing ethylene glycol through dimethyl oxalate hydrogenation, characterized in that the device system comprises a carbonylation reaction system, an esterification reaction system, a purge gas and waste acid coupled recovery system and a hydrogenation reaction system; the carbonylation reaction system comprises a carbonylation reactor, a first gas-liquid separator, a methanol washing tower, a methanol rectification tower and a DMO (dimethyl oxalate) rectification tower; the carbonylation reactor is provided with a top feed inlet, a bottom discharge outlet, a bottom coolant inlet and a top coolant outlet; the first gas-liquid separator is provided with a feed inlet, a gas outlet and a liquid outlet; the methanol washing tower is provided with an upper feed inlet, a lower feed inlet, a top outlet and a bottom outlet; the methanol rectification tower is provided with an upper feed inlet, a lower feed inlet, a top outlet and a bottom outlet; the DMO (dimethyl oxalate) rectification tower is provided with a lower feed inlet, a top outlet and a bottom outlet;

the esterification reaction system comprises an esterification reaction tower and a methanol recovery tower; the esterification reaction tower is provided with a top feed inlet, an upper feed inlet, a plurality of lower feed inlets, a middle reflux inlet, a top outlet and a bottom outlet; the methanol recovery tower is provided with a middle-lower feed inlet, a lower feed inlet, a top outlet and a bottom outlet;

the purge gas and waste acid coupled recovery system comprises a nitric acid concentration tower, an NO (nitric oxide) recovery tower, an MN (methyl nitrite) recovery tower and a pressure swing adsorption tank; the nitric acid concentration tower is provided with a middle feed inlet, a top outlet and a bottom outlet; the NO (nitric oxide) recovery tower is provided with a top feed inlet, a middle feed inlet, a bottom feed inlet, a top outlet and a bottom outlet; the MN (methyl nitrite) recovery tower is provided with an upper feed inlet, a lower feed inlet, a top outlet and a bottom outlet; the pressure swing adsorption tank is provided with a feed inlet, a recovered gas outlet and an exhaust gas outlet;

the hydrogenation reaction system comprises a hydrogenation recycle compressor, a hydrogenation reactor, a second gas-liquid separator, a membrane separator, a methanol separation tower, a light component rectification tower and an ethylene glycol product tower; the hydrogenation recycle compressor comprises an inlet and an outlet; the hydrogenation reactor is provided with a top feed inlet, a bottom discharge outlet, a bottom coolant inlet and a top coolant outlet; the second gas-liquid separator is provided with a feed inlet, a gas outlet and a liquid outlet; the membrane separator is provided with a feed inlet, a recovered gas outlet and an exhaust gas outlet; the methanol separation tower is provided with a middle feed inlet, a top non-condensable gas outlet, a top liquid phase light component outlet and a bottom liquid phase heavy component outlet; the light component rectification tower is provided with a lower feed inlet, a top outlet and a bottom outlet; the ethylene glycol product tower is provided with a lower feed inlet, a top outlet, an upper outlet and a bottom outlet;

the top feed inlet of the carbonylation reactor is connected to a CO raw material pipe and an $N_2$ raw material pipe through a pipeline; the bottom discharge outlet of the carbonylation reactor is connected to the feed inlet of the first gas-liquid separator through a pipeline; the gas outlet of the first gas-liquid separator is connected to the lower feed inlet of the methanol washing tower through a pipeline; the liquid outlet of the first gas-liquid separator is connected to the upper feed inlet of the methanol rectification tower through a pipeline; the top outlet of the methanol washing tower is provided with a branch outlet A and a branch outlet B, the branch outlet A is connected to one lower feed inlet of the esterification reaction tower through a pipeline, and the branch outlet B is connected to the bottom feed inlet of the NO (nitric oxide) recovery tower through a pipeline; the bottom outlet of the methanol washing tower is connected to the lower feed inlet of the methanol rectification tower through a pipeline; the top outlet of the methanol rectification tower is connected to the upper feed inlet of the esterification reaction tower through a pipeline; the bottom outlet of the methanol rectification tower is connected to the lower feed inlet of the DMO (dimethyl oxalate) rectification tower through a pipeline; the bottom outlet of the DMO (dimethyl oxalate) rectification tower is connected to the top feed inlet of the hydrogenation reactor through a pipeline, and the top outlet of the DMO (dimethyl oxalate) rectification tower is a DMC (dimethyl carbonate) product outlet;

the other lower feed inlets of the esterification reaction tower are respectively connected to an NO raw material pipe and a plurality of $O_2$ raw material pipes through pipelines; the top feed inlet of the esterification reaction tower is connected to a methanol raw material pipe through a pipeline; the bottom outlet of the esterification reaction tower is provided with a branch outlet C and a branch outlet D, the branch outlet C is connected to the middle reflux inlet of the esterification reaction tower through a pipeline, and the branch outlet D is connected to the lower feed inlet of the methanol recovery tower through a pipeline; the top outlet of the esterification reaction tower is connected to the top feed inlet of the carbonylation reactor through a pipeline; the top outlet of the methanol recovery tower is provided with a branch outlet E and a branch outlet F, the branch outlet E is connected to the upper feed inlet of the esterification reaction tower through a pipeline, and the branch outlet F is connected to the upper feed inlet of the MN (methyl nitrite) recovery tower through a pipeline; the bottom outlet of the methanol recovery tower is connected to the middle feed inlet of the nitric acid concentration tower through a pipeline;

the top outlet of the nitric acid concentration tower is a waste liquid drain outlet; the bottom outlet of the nitric acid concentration tower is connected to the middle feed inlet of the NO (nitric oxide) recovery tower through a pipeline; the top outlet of the NO (nitric oxide) recovery tower is connected to the lower feed inlet of the MN (methyl nitrite) recovery tower through a pipeline; the bottom outlet of the NO (nitric oxide) recovery tower is connected to the middle-lower feed inlet of the methanol recovery tower through a pipeline; the top outlet of the MN (methyl nitrite) recovery tower is connected to the feed inlet of the pressure swing adsorption tank through a pipeline; the bottom outlet of the MN (methyl nitrite) recovery tower is connected with the upper feed inlet of the esterification reaction tower through a pipeline; the recovered gas outlet of the pressure swing adsorption tank is connected to the top feed inlet of the carbonylation reactor through a pipeline; the exhaust gas outlet of the pressure swing adsorption tank is connected to an external recovery device through a pipeline;

the inlet of the hydrogenation recycle compressor is connected to an industrial hydrogen raw material pipe through a pipeline, and the outlet of the hydrogenation recycle compressor is connected to the top feed inlet of the hydrogenation reactor through a pipeline; the bottom discharge outlet of the hydrogenation reactor is connected to the feed inlet of the second gas-liquid separator through a pipeline; the gas outlet of the second gas-liquid separator is provided with a branch outlet G and a branch outlet H, the branch outlet G is connected to the inlet of the hydrogenation recycle compressor through a pipeline, and the branch outlet H is connected to the feed inlet of the membrane separator through a pipeline; the liquid outlet of the second gas-liquid separator is connected to the lower feed inlet of the methanol separation tower through a pipeline; the top non-condensable gas outlet of the methanol separation tower is connected to the feed inlet of the membrane separator (through a pipeline; the top liquid phase light component outlet of the methanol separation tower is provided with a branch outlet I and a branch outlet J, the branch outlet I is connected to the upper feed inlet of the methanol washing tower through a pipeline, and the branch outlet J is connected to the top feed inlet of the NO (nitric oxide) recovery tower through a pipeline; the bottom liquid phase heavy component outlet of the methanol separation tower is connected to the lower feed inlet of the light component rectification tower through a pipeline; the top light component outlet of the light component rectification tower is connected to an external methanol recovery device through a pipeline; the bottom heavy component outlet of the light component rectification tower is connected to the lower feed inlet of the ethylene glycol product tower through a pipeline; the top outlet of the ethylene glycol product tower is connected to an external 1,2-BDO recovery treatment device through a pipeline; the bottom outlet of the ethylene glycol product tower is connected to an external recovery treatment device through a pipeline; the upper outlet of the ethylene glycol product tower is an ethylene glycol product outlet; and the exhaust gas outlet of the membrane separator is connected to an external recovery device through a pipeline, and the recovered gas outlet of the membrane separator is connected to the top feed inlet of the hydrogenation reactor through a pipeline.

25. The device system for producing dimethyl oxalate through carbonylation of industrial synthesis gas and producing ethylene glycol through dimethyl oxalate hydrogenation according to claim 24, characterized in that the carbonylation reactor is externally connected to a dehydration tower; the dehydration tower is provided with a feed inlet and a dried gas outlet; the top outlet of the esterification reaction tower and the recovered gas outlet of the pressure swing adsorption tank are connected to the feed inlet of the dehydration tower through pipelines; and the dried gas outlet of the dehydration tower is connected to the top feed inlet of the carbonylation reactor through a pipeline.

26. The device system for producing dimethyl oxalate through carbonylation of industrial synthesis gas and producing ethylene glycol through dimethyl oxalate hydrogenation according to claim 25, characterized in that the dehydration tower consists of a molecular sieve dryer A and a molecular sieve dryer B which alternatively run and are regenerated; and the molecular sieve dryer A and the molecular sieve dryer B are packed with adsorbents.

27. The device system for producing dimethyl oxalate through carbonylation of industrial synthesis gas and producing ethylene glycol through dimethyl oxalate hydrogenation according to claim 25, characterized in that the bottom discharge outlet of the carbonylation reactor is connected to an outlet heat exchanger I; the outlet heat exchanger I is provided with a cold material flow inlet, a cold material flow outlet, a hot material flow inlet and a hot material flow outlet; the CO raw material pipe, the $N_2$ raw material pipe and the dried gas outlet of the dehydration tower are connected to the cold material flow inlet of the outlet heat exchanger I through pipelines; the cold material flow outlet of the outlet heat exchanger I is connected to the top feed inlet of the carbonylation reactor through a pipeline; the bottom discharge outlet of the carbonylation reactor is connected to the hot material flow inlet of the outlet heat exchanger I; and the hot material flow outlet of the outlet heat exchanger I is connected to the feed inlet of the first gas-liquid separator through a pipeline.

28. The device system for producing dimethyl oxalate through carbonylation of industrial synthesis gas and producing ethylene glycol through dimethyl oxalate hydrogenation according to claim 27, characterized in that the carbonylation reactor is externally connected to a steam drum I; the steam drum I is provided with a coolant inlet, a coolant outlet, a steam-liquid mixture inlet and a steam outlet; the coolant inlet of the steam drum I is connected to a coolant raw material pipe through a pipeline; the coolant outlet of the steam drum I is connected to the bottom coolant inlet of the carbonylation reactor through a pipeline; the top coolant outlet of the carbonylation reactor is connected to the steam-liquid mixture inlet of the steam drum I through a pipeline; and the steam outlet of the steam drum I is connected to an external steam recovery system through a pipeline.

29. The device system for producing dimethyl oxalate through carbonylation of industrial synthesis gas and producing ethylene glycol through dimethyl oxalate hydrogenation according to claim 28, characterized in that a carbonylation recycle compressor is connected between the branch outlet A of the methanol washing tower and the lower feed inlet of the esterification reaction tower; the carbonylation recycle compressor is provided with an inlet and an outlet; the branch outlet A is connected to the inlet of the carbonylation recycle compressor through a pipeline; and the outlet of the carbonylation recycle compressor is connected to the lower feed inlet of the esterification reaction tower through a pipeline.

30. The device system for producing dimethyl oxalate through carbonylation of industrial synthesis gas and producing ethylene glycol through dimethyl oxalate hydrogenation according to claim 29, characterized in that a compressor is connected between the top outlet of the NO (nitric oxide) recovery tower and the bottom feed inlet of the MN (methyl nitrite) recovery tower; the compressor is provided with an inlet and an outlet; the top outlet of the NO (nitric oxide) recovery tower is connected to the inlet of the compressor through a pipeline; and the outlet of the compressor is connected to the bottom feed inlet of the MN (methyl nitrite) recovery tower through a pipeline.

31. The device system for producing dimethyl oxalate through carbonylation of industrial synthesis gas and producing ethylene glycol through dimethyl oxalate hydrogenation according to claim 30, characterized in that the bottom discharge outlet of the hydrogenation rector is connected to an outlet heat exchanger II; the outlet heat exchanger II is provided with a cold material flow inlet, a cold material flow outlet, a hot material flow inlet and a hot material flow outlet; the bottom outlet of the DMO (dimethyl oxalate) rectification tower, the recovered gas outlet of the membrane separator and the outlet of the hydrogenation recycle compressor are connected to the cold material flow inlet of the outlet heat exchanger II through pipelines; the cold material flow outlet of the outlet heat exchanger II is connected to the top feed inlet of the hydrogenation reactor through a pipeline; the bottom discharge outlet of the hydrogenation reactor is connected to the hot material flow inlet of the outlet heat exchanger II through a pipeline; and the hot material flow outlet of the outlet heat exchanger II is connected to the feed inlet of the second gas-liquid separator through a pipeline.

32. The device system for producing dimethyl oxalate through carbonylation of industrial synthesis gas and producing ethylene glycol through dimethyl oxalate hydrogenation according to claim 31, characterized in that the top feed inlet of the hydrogenation reactor is connected to a startup heater; the startup heater is provided with a feed inlet and a discharge outlet; the cold material flow outlet of the outlet heat exchanger II is connected to the feed inlet of the startup heater through a pipeline; and the discharge outlet of the startup heater is connected to the top feed inlet of the hydrogenation reactor through a pipeline.

33. The device system for producing dimethyl oxalate through carbonylation of industrial synthesis gas and producing ethylene glycol through dimethyl oxalate hydrogenation according to claim 32, characterized in that the hydrogenation reactor is externally connected to a steam drum II; the steam drum II is provided with a coolant inlet, a coolant outlet, a steam-liquid mixture inlet and a steam outlet; the coolant inlet of the steam drum II is connected to a coolant raw material pipe through a pipeline; the coolant outlet of the steam drum II is connected to the bottom coolant inlet of the hydrogenation reactor through a pipeline; the top coolant outlet of the hydrogenation reactor is connected to the steam-liquid mixture inlet of the steam drum II through a pipeline; and the steam outlet of the steam drum II is connected to an external steam recovery system through a pipeline.

34. The device system for producing dimethyl oxalate through carbonylation of industrial synthesis gas and producing ethylene glycol through dimethyl oxalate hydrogenation according to claim 33, characterized in that the second gas-liquid separator comprises a high-pressure gas-liquid separator and a low-pressure gas-liquid separator; the high-pressure gas-liquid separator is provided with a feed inlet, a gas outlet and a liquid outlet; the low-pressure gas-liquid separator is provided with a feed inlet, a gas outlet and a liquid outlet; the bottom discharge outlet of the hydrogenation reactor is connected to the feed inlet of the high-pressure gas-liquid separator through a pipeline; the gas outlet of the high-pressure gas-liquid separator is provided with a branch outlet K and a branch outlet L, the branch outlet K is connected to the inlet of the hydrogenation recycle compressor through a pipeline, and the branch outlet L is connected to the feed inlet of the low-pressure gas-liquid separator through a pipeline; the liquid outlet of the high-pressure gas-liquid separator is connected to the middle feed inlet of the methanol separation tower through a pipeline; the gas outlet of the low-pressure gas-liquid separator is connected to the feed inlet of the membrane separator through a pipeline; and the liquid outlet of the low-pressure gas-liquid separator is connected to the middle feed inlet of the methanol separation tower through a pipeline.

35. The device system for producing dimethyl oxalate through carbonylation of industrial synthesis gas and producing ethylene glycol through dimethyl oxalate hydrogenation according to claim 31, characterized in that a methanol absorption tank is provided before the feed inlet of the membrane separator; the methanol absorption tank is provided with a feed inlet and a purified gas outlet; the gas outlet of the low-pressure gas-liquid separator and the top non-condensable gas outlet of the methanol separation tower are connected to the feed inlet of the methanol absorption tank through pipelines; and the purified gas outlet of the methanol absorption tank is connected to the feed inlet of the membrane separator through a pipeline.

36. The device system for producing dimethyl oxalate through carbonylation of industrial synthesis gas and producing ethylene glycol through dimethyl oxalate hydrogenation according to claim 24, characterized in that the carbonylation reactor is a plate reactor, a tube reactor or a tube-plate combined reactor.

37. The device system for producing dimethyl oxalate through carbonylation of industrial synthesis gas and producing ethylene glycol through dimethyl oxalate hydrogenation according to claim 36, characterized in that the carbonylation reactor is a plate fixed-bed carbonylation reactor; a center of the plate fixed-bed carbonylation reactor is provided with a plate group fixing chamber, a plate group is provided in the plate group fixing chamber and the plate group fixing chamber is further provided with a bottom inlet and a top outlet; a catalyst bed layer is provided between an outer wall of the plate group fixing chamber and an inner wall of the plate fixed-bed carbonylation reactor; the catalyst bed layer is packed with a carbonylation reaction catalyst and the catalyst bed layer is further provided with a top inlet and a bottom outlet; at a bottom of the plate fixed-bed carbonylation reactor, a bottom coolant inlet of the plate fixed-bed carbonylation reactor is connected to the bottom inlet of the plate group fixing chamber through a pipeline, and the bottom outlet of the catalyst bed layer is connected to the bottom discharge outlet of the plate fixed-bed carbonylation reactor through a pipeline; and at a top of the plate fixed-bed carbonylation reactor, a top feed inlet of the plate fixed-bed carbonylation reactor is connected to the top inlet of the catalyst bed layer through a pipeline, and the top outlet of the plate group fixing chamber is connected to a top coolant outlet of the plate fixed-bed carbonylation reactor through a pipeline.

38. The device system for producing dimethyl oxalate through carbonylation of industrial synthesis gas and producing ethylene glycol through dimethyl oxalate hydrogenation according to claim 24, characterized in that the esterification reaction tower is a packing tower or a tower plate-packing combined tower having a tower plate portion and a packing packed portion.

39. The device system for producing dimethyl oxalate through carbonylation of industrial synthesis gas and producing ethylene glycol through dimethyl oxalate hydrogenation according to claim 24, characterized in that the methanol washing tower, the methanol rectification tower, the methanol recovery tower, the NO (nitric oxide) recovery tower, the MN (methyl nitrite) recovery tower, the DMO (dimethyl oxalate) rectification tower and the nitric acid concentration tower are packing towers, plate towers or bubble towers.

40. The device system for producing dimethyl oxalate through carbonylation of industrial synthesis gas and producing ethylene glycol through dimethyl oxalate hydrogenation according to claim 24, characterized in that the hydrogenation reactor is a plate reactor, a tube reactor or a tube-plate combined reactor.

41. The device system for producing dimethyl oxalate through carbonylation of industrial synthesis gas and producing ethylene glycol through dimethyl oxalate hydrogenation according to claim 35, characterized in that the hydrogenation reactor is a plate fixed-bed hydrogenation reactor; a center of the plate fixed-bed hydrogenation reactor is provided with a plate group fixing chamber, a plate group is provided in the plate group fixing chamber and the plate group fixing chamber is further provided with a bottom inlet and a top outlet; a catalyst bed layer is provided between an outer wall of the plate group fixing chamber and an inner wall of the plate fixed-bed hydrogenation reactor; the catalyst bed layer is packed with a hydrogenation reaction catalyst and the catalyst bed layer is further provided with a top inlet and a bottom outlet; at a bottom of the plate fixed-bed hydrogenation reactor, a bottom coolant inlet of the plate fixed-bed hydrogenation reactor is connected to the bottom inlet of the plate group fixing chamber through a pipeline, and the bottom outlet of the catalyst bed layer is connected to the bottom discharge outlet of the plate fixed-bed hydrogenation reactor through a pipeline; and at a top of the plate fixed-bed hydrogenation reactor, a top feed inlet of the plate fixed-bed hydrogenation reactor is connected to the top inlet of the catalyst bed layer through a pipeline, and the top outlet of the plate group fixing chamber is connected to a top coolant outlet of the plate fixed-bed hydrogenation reactor through a pipeline.

42. The device system for producing dimethyl oxalate through carbonylation of industrial synthesis gas and producing ethylene glycol through dimethyl oxalate hydrogenation according to claim 24, characterized in that the membrane separator consists of 1-100 hollow fiber membrane modules connected in parallel or in series.

\* \* \* \* \*